US010745732B2

(12) United States Patent
Kim et al.

(10) Patent No.: US 10,745,732 B2
(45) Date of Patent: Aug. 18, 2020

(54) GENETIC MARKER FOR DISCRIMINATING AND DETECTING CAUSATIVE BACTERIA OF FISH EDWARDSIELLOSIS AND STREPTOCOCCOSIS, AND METHOD FOR DISCRIMINATING AND DETECTING CAUSATIVE BACTERIA USING SAME

(71) Applicant: National Institute of Fisheries Science, Busan (KR)

(72) Inventors: Myoung Sug Kim, Busan (KR); Sung-Hee Jung, Busan (KR); Hye Sung Choi, Gyeongsangnam-do (KR); Hyun-Ja Han, Busan (KR); Jeung-Wan Do, Busan (KR); Jin-Do Kim, Jeollanam-do (KR)

(73) Assignee: NATIONAL INSTITUTE OF FISHERIES SCIENCE, Busan (KR)

( * ) Notice: Subject to any disclaimer, the term of this patent is extended or adjusted under 35 U.S.C. 154(b) by 88 days.

(21) Appl. No.: 15/571,442

(22) PCT Filed: Dec. 6, 2016

(86) PCT No.: PCT/KR2016/014215
§ 371 (c)(1),
(2) Date: Nov. 2, 2017

(87) PCT Pub. No.: WO2017/099445
PCT Pub. Date: Jun. 15, 2017

(65) Prior Publication Data
US 2018/0127798 A1 May 10, 2018

(30) Foreign Application Priority Data
Dec. 11, 2015 (KR) .................. 10-2015-0176870

(51) Int. Cl.
| C07H 21/04 | (2006.01) |
| C12Q 1/68 | (2018.01) |
| C12Q 1/04 | (2006.01) |
| C12Q 1/689 | (2018.01) |
| C12Q 1/6809 | (2018.01) |
| C12Q 1/6888 | (2018.01) |
| G01N 33/569 | (2006.01) |

(52) U.S. Cl.
CPC ............... *C12Q 1/04* (2013.01); *C12Q 1/689* (2013.01); *C12Q 1/6809* (2013.01); *C12Q 1/6888* (2013.01); *G01N 33/56911* (2013.01); *C12Q 2525/107* (2013.01); *C12Q 2527/107* (2013.01); *G01N 2800/26* (2013.01)

(58) Field of Classification Search
None
See application file for complete search history.

(56) References Cited

U.S. PATENT DOCUMENTS 8,889,358 B2 11/2014 Rudi et al.
2007/0059693 A1 3/2007 Miller et al.

FOREIGN PATENT DOCUMENTS

KR 10-1531296 B1 6/2015
KR 10-1644773 B1 8/2016

OTHER PUBLICATIONS

Guosi et al. (Acta Oceanol. Sin. vol. 31, No. 4, pp. 140-148, 2012) (Year: 2012).*
Genbank AB682263 (Nakagawa, Jan. 28, 2012). (Year: 2012).*
Chen, S., et al., "Lactococcus Garvieae Infection in the Giant Freshwater Prawn *Macrobranchium rosenbergii* Confirmed by Polymerase Chain Reaction and 16S rDNA Sequencing", "Diseases of Aquatic Organisms", 2001, pp. 45-52, vol. 45.
Genbank, "*Streptococcus iniae* Strain TSG004 16S Ribosomal RNA Gene, Partial Sequence", "GenBank KF826094.3", Aug. 5, 2015.
Genbank, "*Streptococcus parauberis* Strain PLB-2 16S Ribosomal RNA Gene, Partial Sequence", "GenBank KT825567.1", Oct. 6, 2015.
Genbank, "Lactococcus Garvieae Strain LIPOA/UEL_56 16S Ribosomal RNA Gene, Partial Sequence", "GenBank KU173113.1", Nov. 30, 2015.
Genbank, "*Streptococcus iniae* Strain TOS08 16S Ribosomal RNA, Partial Sequence", "GenBank KP729644.2", Aug. 3, 2015.
Genbank, "*Streptococcus iniae* Strain TOS07 16S Ribosomal RNA Gene, Partial Sequence", "GenBank 729643.2", Aug. 3, 2015.
Hassan, A., et al., "Evaluation of PCR Methods for Rapid Identification and Differentiation of *Streptococcus uberis* and *Streptococcus parauberis*", "Journal of Clinical Microbiology", Apr. 2001, pp. 1618-1621, vol. 39, No. 4.

(Continued)

*Primary Examiner* — Jeanine A Goldberg
(74) *Attorney, Agent, or Firm* — Hultquist, PLLC; Steven J. Hultquist

(57) ABSTRACT

The present disclosure relates to genetic markers for discrimination and detection of bacteria causing Edwardsiellosis and Streptococcosis in fish, and a method for discriminating and detecting the bacteria using the same. A genetic marker for discrimination and/or detection of each of *Edwardsiella tarda*, *Streptococcus iniae*, *Streptococcus parauberis* and *Lactococcus garvieae*, which cause fish diseases, is selected and a peptide nucleic acid and a primer pair, which are specific for the genetic marker, are used to amplify and obtain melting curves having different fluorescences depending on bacterial species. Thus, bacteria that cause fish diseases can be discriminated and whether or not fish would be infected with the bacteria can be detected in a simple, rapid and accurate manner.

3 Claims, 13 Drawing Sheets
(13 of 13 Drawing Sheet(s) Filed in Color)
Specification includes a Sequence Listing.

(56) References Cited

OTHER PUBLICATIONS

Lan, J., et al., "Isolation of an unusual strain of Edwardsiella tarda from turbot and establish a PCR detection technique with the gyrB gene", "Journal of Applied Microbiology", 2008, pp. 644-651, vol. 105.

Park, S. B., et al., "Development of a multiplex PCR assay to detect Edwardsiella tarda, *Streptococcus parauberis*, and *Streptococcus iniae* in olive Flounder (*Paralichthys olivaceus*)", "Journal of Veterinary Science", 2014, pp. 163-166, vol. 15, No. 1.

Note: For the non-patent literature citations that no month of publication is indicated, the year of publication is more than 1 year prior to the effective filing date of the present application.

* cited by examiner

SEQUENCE LISTING

<160> NUMBER OF SEQ ID NOS: 51

<210> SEQ ID NO 1
<211> LENGTH: 20
<212> TYPE: DNA
<213> ORGANISM: Artificial Sequence
<220> FEATURE:
<223> OTHER INFORMATION: Universal forward Primer(27F)

<400> SEQUENCE: 1
agagtttgat cctggctcag         20

<210> SEQ ID NO 2
<211> LENGTH: 18
<212> TYPE: DNA

```
<213> ORGANISM: Artificial Sequence
<220> FEATURE:
<223> OTHER INFORMATION: Reverse primer

<400> SEQUENCE: 2
gggttcatct gatggcat                                                 18

<210> SEQ ID NO 3
<211> LENGTH: 18
<212> TYPE: DNA
<213> ORGANISM: Artificial Sequence
<220> FEATURE:
<223> OTHER INFORMATION: Universal reverse primer

<400> SEQUENCE: 3
tagccgtccc tttctggt                                                 18

<210> SEQ ID NO 4
<211> LENGTH: 14
<212> TYPE: DNA
<213> ORGANISM: Artificial Sequence
<220> FEATURE:
<223> OTHER INFORMATION: PNA 1

<400> SEQUENCE: 4
acgtcgcaag acca                                                     14

<210> SEQ ID NO 5
<211> LENGTH: 14
<212> TYPE: DNA
<213> ORGANISM: Artificial Sequence
<220> FEATURE:
<223> OTHER INFORMATION: PNA 2

<400> SEQUENCE: 5
ctagagtaca catg                                                     14

<210> SEQ ID NO 6
<211> LENGTH: 14
<212> TYPE: DNA
<213> ORGANISM: Artificial Sequence
<220> FEATURE:
<223> OTHER INFORMATION: PNA 3

<400> SEQUENCE: 6
aagactggtg cttg                                                     14

<210> SEQ ID NO 7
<211> LENGTH: 14
<212> TYPE: DNA
<213> ORGANISM: Artificial Sequence
<220> FEATURE:
<223> OTHER INFORMATION: PNA 4

<400> SEQUENCE: 7
aatctgccga gtag                                                     14

<210> SEQ ID NO 8
<211> LENGTH: 14
<212> TYPE: DNA
<213> ORGANISM: Artificial Sequence
<220> FEATURE:
<223> OTHER INFORMATION: Edwardsiella tarda_16S rDNA marker

<400> SEQUENCE: 8
tggtcttgcg acgt                                                     14
```

```
<210> SEQ ID NO 9
<211> LENGTH: 14
<212> TYPE: DNA
<213> ORGANISM: Artificial Sequence
<220> FEATURE:
<223> OTHER INFORMATION: Streptococcus iniae_16S rDNA marker

<400> SEQUENCE: 9
catgtgtact ctag                                                         14

<210> SEQ ID NO 10
<211> LENGTH: 14
<212> TYPE: DNA
<213> ORGANISM: Artificial Sequence
<220> FEATURE:
<223> OTHER INFORMATION: Streptococcus parauberis_16S rDNA marker

<400> SEQUENCE: 10
caagcaccag tctt                                                         14

<210> SEQ ID NO 11
<211> LENGTH: 14
<212> TYPE: DNA
<213> ORGANISM: Artificial Sequence
<220> FEATURE:
<223> OTHER INFORMATION: Lactococcus garvieae_16S rDNA marker

<400> SEQUENCE: 11
ctactcggca gatt                                                         14

<210> SEQ ID NO 12
<211> LENGTH: 398
<212> TYPE: DNA
<213> ORGANISM: Vibrio alginolyticus
<220> FEATURE:
<221> NAME/KEY: misc_feature
<222> LOCATION: (1)..(398)
<223> OTHER INFORMATION: Cons_V.alginolyticus/1-1509

<400> SEQUENCE: 12
ttaatcatgg ctcagattga acgctggcgg caggcctaac acatgcaagt cgagcggaaa       60
cgagttatct gaaccttcgg ggatatctga accttcgggg aacgataacg gcgtcgagcg      120
gcggacgggt gagtaatgcc taggaaattg ccctgatgtg gtgggggata accattggaa      180
acgatggcta ataccgcatg atgcctacgg gccaaagagg gggaccttcg ggccactttc      240
agtcgtgagg aaggtggtgt agttaatagc tgcattattt gacgttagcg acagaagaag      300
caccggctaa ctccgggcct ctcgcgtcag gatatgccta ggtgggatta gctagttggt      360
gaggtaaggg ctcaccaagg cgacgatccc tagctggt                              398

<210> SEQ ID NO 13
<211> LENGTH: 374
<212> TYPE: DNA
<213> ORGANISM: Vibrio natriegens
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (1)..(374)
<223> OTHER INFORMATION: Cons_V.natrigens/1-1460
<220> FEATURE:
<221> NAME/KEY: misc_feature
<222> LOCATION: (4)..(4)
```

```
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 13
nnangnggcn ggnctacaca tgcaagtcga gcggaacgag ttatctgaac cttcggggt      60 atctgaacct tcgggggacg ataacggcgt cgagcggcgg acgggtgagt aatgcctagg    120
aaattgccct gatgtggtgg gggataacca ttggaaacga tggctaatac cgcatgatgc    180
ctacgggcca agagggggga ccttcgggcc actttcagtc gtgaggaagg tagtgtagtt    240
aatagctgca ttatttgacg ttagcgacag aagaagcacc ggctaactcc gggcctctcg    300
cgtcaggata tgcctaggtg ggattagcta gttggtgagg taagggctca ccaaggcgac    360
gatccctagc tggt                                                      374

<210> SEQ ID NO 14
<211> LENGTH: 393
<212> TYPE: DNA
<213> ORGANISM: Vibrio parahaemolyticus
<220> FEATURE:
<221> NAME/KEY: misc_feature
<222> LOCATION: (1)..(393)
<223> OTHER INFORMATION: Cons_V.parahaemolyticus/1-1497
<220> FEATURE:
<221> NAME/KEY: misc_feature
<222> LOCATION: (65)..(66)
<223> OTHER INFORMATION: n is a, c, g, or t
<220> FEATURE:
<221> NAME/KEY: misc_feature
<222> LOCATION: (68)..(68)
<223> OTHER INFORMATION: n is a, c, g, or t
<220> FEATURE:
<221> NAME/KEY: misc_feature
<222> LOCATION: (77)..(78)
<223> OTHER INFORMATION: n is a, c, g, or t
<220> FEATURE:
<221> NAME/KEY: misc_feature
<222> LOCATION: (83)..(84)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t
<220> FEATURE:
<221> NAME/KEY: misc_feature
<222> LOCATION: (95)..(97)
<223> OTHER INFORMATION: n is a, c, g, or t

<400> SEQUENCE: 14
catggctcag attgaacgct ggcggcaggc ctaacacatg caagtcgagc ggaaacgagt     60
tatcnnancc ttcgggnnta tcnnanccat cgggnnncga taacggcgtc gagcggcgga   120
cgggtgagta atgcctagga aattgccctg atgtggtggg ggataaccat tggaaacgat   180
ggctaatacc gcatgatgcc tacgggccaa agagggggac cttcgggcca ctttcagtcg   240
tgaggaaggt agtgtagtta atagctgcat tatttgacgt tagcgacaga agaagcaccg   300
gctaactccg ggcctctcgc gtcaggatat gcctaggtgg gattagctag ttggtgaggt   360
aagggctcac caaggcgacg atccctagct ggt                                393
```

<210> SEQ ID NO 15
<211> LENGTH: 391
<212> TYPE: DNA
<213> ORGANISM: Vibrio harveyi
<220> FEATURE:
<221> NAME/KEY: misc_feature
<222> LOCATION: (1)..(391)
<223> OTHER INFORMATION: Cons_V.harvey/1-1490

<400> SEQUENCE: 15

| | | | | | | |
|---|---|---|---|---|---|---|
| tggctcagat | tgaacgctgg | cggcaggcct | aacacatgca | agtcgagcgg | aaacgagtta | 60 |
| tctgaacctt | cggggatatc | tgaaccttcg | gggaacgata | acggcgtcga | gcggcggacg | 120 |
| ggtgagtaat | gcctaggaaa | ttgccctgat | gtggtgggg | ataaccattg | aaacgatgg | 180 |
| ctaataccgc | ataataccttt | cgggtcaaag | aggggaccttt | cgggccact | ttcagtcgtg | 240 |
| aggaaggtag | tgtagttaat | agctgcatta | tttgacgtta | gcgacagaag | aagcaccggc | 300 |
| taactccggg | cctctcgcgt | caggatatgc | ctaggtggga | ttagctagtt | ggtgaggtaa | 360 |
| tggctcacca | aggcgacgat | ccctagctgg | t | | | 391 |

<210> SEQ ID NO 16
<211> LENGTH: 399
<212> TYPE: DNA
<213> ORGANISM: Vibrio rotiferianus
<220> FEATURE:
<221> NAME/KEY: misc_feature
<222> LOCATION: (1)..(399)
<223> OTHER INFORMATION: Cons_V.rotiferianus/1-1501

<400> SEQUENCE: 16

| | | | | | | |
|---|---|---|---|---|---|---|
| tttgatcatg | gctcagattg | aacgctggcg | gcaggcctaa | cacatgcaag | tcgagcggaa | 60 |
| acgagttatc | tgaaccttcg | ggatatctg | aaccttcggg | gaacgataac | ggcgtcgagc | 120 |
| ggcggacggg | tgagtaatgc | ctaggaaatt | gccctgatgt | ggtggggat | aaccattgga | 180 |
| aacgatggct | aataccgcat | aataccttcg | gtcaaagag | gggaccttc | gggccacttt | 240 |
| cagtcgtgag | gaaggtggta | gtgttaatag | cactatcatt | tgacgttagc | gacagaagaa | 300 |
| gcaccggcta | actccgggcc | tctcgcgtca | ggatatgcct | aggtgggatt | agctagttgg | 360 |
| tgaggtaatg | gctcaccaag | gcgacgatcc | ctagctggt | | | 399 |

<210> SEQ ID NO 17
<211> LENGTH: 391
<212> TYPE: DNA
<213> ORGANISM: Vibrio shilonii
<220> FEATURE:
<221> NAME/KEY: misc_feature
<222> LOCATION: (1)..(391)
<223> OTHER INFORMATION: Cons_V.shilonii/1-1479
<220> FEATURE:
<221> NAME/KEY: misc_feature
<222> LOCATION: (267)..(267)
<223> OTHER INFORMATION: n is a, c, g, or t

<400> SEQUENCE: 17

| | | | | | | |
|---|---|---|---|---|---|---|
| tggctcagat | tgaacgctgg | cggcaggcct | aacacatgca | agtcgagcgg | aaacgagtta | 60 |
| actgaacctt | cggggataac | tgaaccttcg | ggaacgtta | acggcgtcga | gcggcggacg | 120 |
| ggtgagtaat | gcctgggaaa | ttgccctgat | gtggtgggg | ataaccattg | aaacgatgg | 180 |
| ctaataccgc | ataatagctt | cggctcaaag | aggggaccct | cgggccact | ttcagcagtg | 240 |
| aggaaggtgg | gtatgttaat | agcatantca | tttgacgtta | gctgcagaag | aagcaccggc | 300 |

```
taactccggg cctctcgcgt caggatatgc ccaggtggga ttagctagtt ggtgaggtaa    360
tggctcacca aggcgacgat ccctagctgg t                                  391

<210> SEQ ID NO 18
<211> LENGTH: 393
<212> TYPE: DNA
<213> ORGANISM: Vibirio ponticus
<220> FEATURE:
<221> NAME/KEY: misc_feature
<222> LOCATION: (1)..(393)
<223> OTHER INFORMATION: Cons_V.ponticus/1-1449

<400> SEQUENCE: 18
catggctcag attgaacgct ggcggcaggc ctaacacatg caagtcgagc ggcagcgaca    60
acattgaacc ttcggggggac attgaaccett cggggattt gttgggcggc gagcggcgga  120
cgggtgagta atgcctagga aattgccctg atgtggtggg gataaccat tggaaacgat   180 ggctaatacc gcatgatgcc tacgggccaa agaggggac cttcgggcca ctttcagtag    240
ggaggaaggt tcatgcgtta atagcgtatg gatttgacgt tacctacaga agaagcaccg   300
gctaactccg ggcctctcgc gtcaggatat gcctaggtgg gattagctag ttggtgaggt   360
aagggctcac caaggcgacg atccctagct ggt                                393

<210> SEQ ID NO 19
<211> LENGTH: 391
<212> TYPE: DNA
<213> ORGANISM: Vibrio crassostreae
<220> FEATURE:
<221> NAME/KEY: misc_feature
<222> LOCATION: (1)..(391)
<223> OTHER INFORMATION: Cons_V.crassostreae/1-1491

<400> SEQUENCE: 19
tggctcagat tgaacgctgg cggcaggcct aacacatgca agtcgagcgg aaacgacact   60
aacaatcctt cgggtgctaa caatccttcg ggtgcgttaa tgggcgtcga gcggcggacg   120
ggtgagtaat gcctaggaaa ttgccttgat gtggtggggg ataaccattg gaaacgatgg   180
ctaataccgc ataatgccta cgggccaaag aggggaccct tcgggccact ttcagttgtg   240 aggaagggg tagtgttaat agcgctatct cttgacgtta gcaacagaag aagcaccggc   300
taactccggg cctctcgcgt caagatatgc ctaggtggga ttagctagtt ggtgaggtaa   360
tggctcacca aggcgacgat ccctagctgg t                                  391

<210> SEQ ID NO 20
<211> LENGTH: 402
<212> TYPE: DNA
<213> ORGANISM: Vibrio gigantis
<220> FEATURE:
<221> NAME/KEY: misc_feature
<222> LOCATION: (1)..(402)
<223> OTHER INFORMATION: Cons_V.gigantis/1-1507

<400> SEQUENCE: 20
agagtttgga taggctcaga ttgaacgctg gcggcaggcc taacacatgc aagtcgagcg    60
gaaacgacac taacaatcct tcgggtgcta acaatccttc gggtgcgtta atgggcgtcg   120
agcggcggac gggtgagtaa tgcctaggaa attgccttga tgtggtgggg gataaccatt   180
ggaaacgatg gctaataccg cataatgcct acgggccaaa gaggggacc ttcgggccac    240 tttcagttgt gaggaagggg gtagcgttaa tagcgctatc tcttgacgtt agcaacagaa   300
gaagcaccgg ctaactccgg gcctctcgcg tcaagatatg cctaggtggg attagctagt   360
```

```
tggtgaggta atggctcacc aaggcgacga tccctagctg gt         402
```

<210> SEQ ID NO 21
<211> LENGTH: 393
<212> TYPE: DNA
<213> ORGANISM: Vibrio pomeroyi
<220> FEATURE:
<221> NAME/KEY: misc_feature
<222> LOCATION: (1)..(393)
<223> OTHER INFORMATION: Cons_V.pomeroyi/1-1489

<400> SEQUENCE: 21

```
catggctcag attgaacgct ggcggcaggc ctaacacatg caagtcgagc ggaaacgaca    60
ctaacaatcc ttcgggtgct aacaatcctt cgggtgcgtt aatgggcgtc gagcggcgga   120
cgggtgagta atgcctagga aattgccttg atgtggtggg ggataaccat tggaaacgat   180
ggctaatacc gcataatgcc tacgggccaa agaggggac cttcgggcca ctttcagttg    240
tgaggaaggg ggtgtagtta atagctgcat ctcttgacgt tagcaacaga agaagcaccg   300
gctaactccg ggcctctcgc gtcaagatat gcctaggtgg gattagctag ttggtgaggt   360
aatggctcac caaggcgacg atccctagct ggt                                393
```

<210> SEQ ID NO 22
<211> LENGTH: 393
<212> TYPE: DNA
<213> ORGANISM: Vibrio splendidus
<220> FEATURE:
<221> NAME/KEY: misc_feature
<222> LOCATION: (1)..(393)
<223> OTHER INFORMATION: Cons_V.splendidus/1-1494
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (79)..(79)
<223> OTHER INFORMATION: n is a, c, g, or t
<220> FEATURE:
<221> NAME/KEY: misc_feature
<222> LOCATION: (269)..(269)
<223> OTHER INFORMATION: n is a, c, g, or t

<400> SEQUENCE: 22

```
catggctcag attgaacgct ggcggcaggc ctaacacatg caagtcgagc ggaaacgaca    60
ntattgattc ttcggaggnt attgattctt cggaggattt aatgggcgtc gagcggcgga   120
cgggtgagta atgcctagga aattgccttg atgtggtggg ggataaccat tggaaacgat   180
ggctaatacc gcataatgcc tacgggccaa agaggggat cttcggacca ctttcagttg    240
tgaggaaggg tgtgtagtta atagctgcnc atcttgacgt tagcaacaga agaagcaccg   300
gctaactccg gacctctcgc gtcaagatat gcctaggtgg gattagctag ttggtgaggt   360
aatggctcac caaggcgacg atccctagct ggt                                393
```

<210> SEQ ID NO 23
<211> LENGTH: 374
<212> TYPE: DNA
<213> ORGANISM: Vibrio tapetis
<220> FEATURE:
<221> NAME/KEY: misc_feature
<222> LOCATION: (1)..(374)
<223> OTHER INFORMATION: Cons_V.tapetis/1-1465
<220> FEATURE:
<221> NAME/KEY: misc_feature
<222> LOCATION: (12)..(13)

```
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (33)..(35)
<223> OTHER INFORMATION: n is a, c, g, or t

<400> SEQUENCE: 23
gctcagattg anngctgggng gcaggcctan cannngcaag tcgagcggaa acgagaagta      60
gcttgctaag tagcttgcta cttcggcgtc gagcggcgga cgggtgagta atgcctagga     120
aattgccctg atgtggtggg ggataaccat tggaaacgat ggctaatacc gcataatgcc     180
ttcgggccaa agaggggac  cttcgggcca ctttcagcag tgaggaaagg ggtgtacgtt     240
aatagcgtgc atccttgacg ttagctgcag aagaagcacc ggctaactcc gggcctctcg     300
cgtcaggata tgcctaggtg ggattagcta gttggtgagg taatggctca ccaaggcgac     360
gatccctagc tggt                                                       374

<210> SEQ ID NO 24
<211> LENGTH: 377
<212> TYPE: DNA
<213> ORGANISM: Vibrio anguillarum
<220> FEATURE:
<221> NAME/KEY: misc_feature
<222> LOCATION: (1)..(377)
<223> OTHER INFORMATION: Cons_V.anguillarum/1-1478

<400> SEQUENCE: 24
catggctcag attgaacgct ggcggcaggc ctaacacatg caagtcgagc ggcagcacag      60
aggaacttgt tgaggaactt gttccttggg tggcgagcgg cggacgggtg agtaatgcct     120
aggaaattgc cctgatgtgg tggggataa  ccattggaaa cgatggctaa taccgcatga     180
tgcctacggg ccaaagaggg ggaccttcgg gccactttca gtcgtgagga aggtggtgtt     240
gttaatagca gcatcatttg acgttagcga cagaagaagc accggctaac tccgggcctc     300
tcgcgtcagg atatgcctag gtgggattag ctagttggtg aggtaatggc tcaccaaggc     360
gacgatccct agctggt                                                    377

<210> SEQ ID NO 25
<211> LENGTH: 389
<212> TYPE: DNA
<213> ORGANISM: Vibrio ichtyoenteri
<220> FEATURE:
<221> NAME/KEY: misc_feature
<222> LOCATION: (1)..(389)
<223> OTHER INFORMATION: Cons_V.ichtyoenteri/1-1514

<400> SEQUENCE: 25
agagttttga tcatggctca gattgaacgc tggcggcagg cctaacacat gcaagtcgag      60
cggtaacaga gagaaagctt ggagaaagct tgctttcttt gctgacgagc ggcggacggg     120
tgagtaatgc ctgggaatat gccttgatgt ggtgggggat aaccattgga aacgatggct     180
aataccgcat aatgcctacg ggccaaagag gggatcttc  ggaccacttt cagtcgtgag     240
gaaggtagtt gcgttaatag cgtaattatt tgacgttagc gacagaagaa gcaccggcta     300
actccggacc tctcgcgtca agattagccc aggtgggatt agctagttgg tgaggtaatg     360
```

```
gctcaccaag gcgacgatcc ctagctggt                                         389
```

<210> SEQ ID NO 26
<211> LENGTH: 376
<212> TYPE: DNA
<213> ORGANISM: Vibrio scophthalmi
<220> FEATURE:
<221> NAME/KEY: misc_feature
<222> LOCATION: (1)..(376)
<223> OTHER INFORMATION: Cons_V.scophthalmi/1-1464

<400> SEQUENCE: 26

```
tggctcagat tgaacgctgg cggcaggcct aacacatgca agtcgagcgg taacagagag       60
aaagcttgga gaaagcttgc tttctttgct gacgagcggc ggacgggtga gtaatgcctg      120
ggaatatgcc ttgatgtggt gggggataac cattggaaac gatggctaat accgcataat     180
gcctacgggc aaagagggg gatcttcgga ccactttcag tcgtgaggaa ggtagttgcg      240
ttaatagcgt aattatttga cgttagcgac agaagaagca ccggctaact ccggacctct     300
cgcgtcaaga ttagcccagg tgggattagc tagttggtga ggtaatggct caccaaggcg    360
acgatcccta gctggt                                                      376
```

<210> SEQ ID NO 27
<211> LENGTH: 373
<212> TYPE: DNA
<213> ORGANISM: Vibrio vulnificus
<220> FEATURE:
<221> NAME/KEY: misc_feature
<222> LOCATION: (1)..(373)
<223> OTHER INFORMATION: Cons_V.vulnificus/1-1482

<400> SEQUENCE: 27

```
atggctcaga ttgaacgctg gcggcaggcc taacacatgc aagtcgagcg gcagcacaga      60
gaaacttgga gaaacttgtt tctcgggtgg cgagcggcgg acgggtgagt aatgcctggg    120
aaattgccct gatgtgtggg ggataaccat tggaaacgat ggctaatacc gcatgatagc    180
ttcggctcaa gaggggggac cttcgggcca ctttcagtcg tgaggaaggt ggtagtgtta    240
atagcactat catttgacgt tagcgacaga agaagcaccg ctaactccg gcctctcgc      300
gtcaggatat gcccaggtgg gattagctag ttggtgaggt aagggctcac caaggcgacg    360
atccctagct ggt                                                        373
```

<210> SEQ ID NO 28
<211> LENGTH: 409
<212> TYPE: DNA
<213> ORGANISM: Aliivibrio sp.
<220> FEATURE:
<221> NAME/KEY: misc_feature
<222> LOCATION: (1)..(409)
<223> OTHER INFORMATION: Cons_Aliivibrio/1-1526
<220> FEATURE:
<221> NAME/KEY: misc_feature
<222> LOCATION: (9)..(10)
<223> OTHER INFORMATION: n is a, c, g, or t
<220> FEATURE:
<221> NAME/KEY: misc_feature
<222> LOCATION: (32)..(34)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t

<400> SEQUENCE: 28

```
cagagttttnn acatggctca gattgaacgc tnnnanggcg gcaggcctaa cacatgcaag    60
tcgagcggaa acgacttaac tgaaccttcg gggataactg aaccttcggg aacgttaag    120 ggcgtcgagc ggcggacggg tgagtaatgc ctgggaatat gccttagtgt ggtgggggat   180
aactattgga aacgatagct aataccgcat aatgtcttcg gaccaaagag ggggaccttc   240
gggccacttt cagtagggag gaaggtgttt tagttaatag cttctgcatt tgacgttacc   300
tacagaagaa gcaccggcta actccgggcc tctcgcgcta agattagccc aggtgagatt   360
agctagttgg tgaggtaaga gctcaccaag gcgacgatct ctagctggt              409
```

```
<210> SEQ ID NO 29
<211> LENGTH: 391
<212> TYPE: DNA
<213> ORGANISM: Vibrio fischeri
<220> FEATURE:
<221> NAME/KEY: misc_feature
<222> LOCATION: (1)..(391)
<223> OTHER INFORMATION: Cons_V.fischeri/1-1494

<400> SEQUENCE: 29
```

```
tggctcagat tgaacgctgg cggcaggcct aacacatgca agtcgagcgg aaacgactta    60
actgaacctt cggggataac tgaaccttcg ggaacgttaa aggcgtcga gcggcggacg   120 ggtgagtaat gcctgggaat atgccttagt gtggtgggg ataactattg aaacgatag    180 ctaataccgc ataatgtctt cggaccaaag aggggaccct tcgggccact ttcagtaggg   240
aggaaggttc atacgttaat agcgtatgga tttgacgtta cctacagaag aagcaccggc   300
taactccggg cctctcgcgc taagattagc ccaggtgaga ttagctagtt ggtgaggtaa   360
gagctcacca aggcgacgat ctctagctgg t                                  391
```

```
<210> SEQ ID NO 30
<211> LENGTH: 361
<212> TYPE: DNA
<213> ORGANISM: Vibrio logei
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (1)..(361)
<223> OTHER INFORMATION: Cons_V.logei/1-1089

<400> SEQUENCE: 30
```

```
nnnnagggcg gcagctacac atgcaagtcg agcggtaaca ggaattagct tgctaattta    60
gcttgctaat tcgctgacga gcggcggacg ggtgagtaat gcctgggaat atgccttgat   120
gtggtggggg ataactattg aaacgatag ctaataccgc ataatgtctt cggaccaaag    180 aggggatct tcggaccact ttcagtcgtg aggaagggtg tgtagttaat agctgcatat    240
cttgacgtta gcgacagaag aagcaccggc taactccgga cctctcgcgc caagattagc   300
ccaggtgaga ttagctagtt ggtgaggtaa gagctcacca aggcgacgat ctctagctgg   360
t                                                                   361
```

```
<210> SEQ ID NO 31
<211> LENGTH: 390
<212> TYPE: DNA
<213> ORGANISM: Photobacterium damselae
<220> FEATURE:
<221> NAME/KEY: misc_feature
<222> LOCATION: (1)..(390)
<223> OTHER INFORMATION: Cons_P.damselae/1-1483
```

<400> SEQUENCE: 31

```
ggctcagatt gaacgctggc ggcaggccta acacatgcaa gtcgagcggc agcgacttaa      60
ctgaaccttc ggggataact gaaccttcgg ggaacgttaa gggcggcgag cggcggacgg     120
gtgagtaatg cctgggaata tgccctgatg tggtggggga taactattgg aaacgatagc    180
taataccgca taatctcttc ggagcaaaga gggggacctt cgggccactt tcagtaggga    240
ggaaggtagt gtagttaaca cctgcattat ttgacgttac ctacagaaga agcaccggct    300
aactccgggc ctctcgcgtc aggattagcc caggtgggat tagcttgttg gtgaggtaat    360
ggctcaccaa ggcaacgatc cctagctggt                                     390
```

<210> SEQ ID NO 32
<211> LENGTH: 393
<212> TYPE: DNA
<213> ORGANISM: Enterovibrio sp.
<220> FEATURE:
<221> NAME/KEY: misc_feature
<222> LOCATION: (1)..(393)
<223> OTHER INFORMATION: Cons_Enterovibrio/1-1500

<400> SEQUENCE: 32

```
tggctcagat tgaacgctgg cggcaggcct aacacatgca agtcgagcgg cagcgacaac      60
atctgactct tcggaggaca tctgactctt cggaggactt gttgggcggc gagcggcgga    120
cgggtgagta atggctggga acctgcccga tagaggaggg ggataacagt tggaaacgac    180
tgctaatacc gcatgatgtc tacgaccaa aggaggggga cttcggacca ctttcagcag    240
tgaggaaggt tacgtagtta atacctgcgt gatttgacgt tagctgcaga agaagcaccg    300
gctaactccg gacctttcgc tatcggatgg gcccagttgg gattagctag ttggtgaggt    360
aatggctcac caaggcgacg atccctagct ggt                                  393
```

<210> SEQ ID NO 33
<211> LENGTH: 375
<212> TYPE: DNA
<213> ORGANISM: Photobacterium sp.
<220> FEATURE:
<221> NAME/KEY: misc_feature
<222> LOCATION: (1)..(375)
<223> OTHER INFORMATION: Cons_Photobacterium_other/1-1477

<400> SEQUENCE: 33

```
tggctcagat tgaacgctgg cggcaggcct aacacatgca agtcgagcgg taacagaaag      60
aaagcttgag aaagcttgct ttctttgctg acgagcggcg gacgggtgag taatgcctgg    120
gaatataccc tgatgtggtg ggggataact attggaaacg atagctaata ccgcataatc    180
tcttcggagc aaagaggggg accttcgggc cactttcagt gtgaggaag gcagttaagt     240 taatagctta gctgtttgac gttagcaaca gaagaagcac cggctaactc cgggcctctc    300
gcgtcaggat tagcccaggt gggattagct agttggtggg gtaatggctc accaaggcga    360
cgatccctag ctggt                                                     375
```

<210> SEQ ID NO 34
<211> LENGTH: 375
<212> TYPE: DNA
<213> ORGANISM: Aeromonas sp.
<220> FEATURE:
<221> NAME/KEY: misc_feature
<222> LOCATION: (1)..(375)
<223> OTHER INFORMATION: Cons_Aeromonas/1-1458

<400> SEQUENCE: 34

```
catggctcag attgaacgct ggcggcaggc ctaacacatg caagtcgagc ggcagcggga      60
aagtagcttg gtagcttgct acttttgccg gcgagcggcg gacgggtgag taatgcctgg     120
ggatctgccc agtcgaggag ggggataact actggaaacg gtagctaata ccgcatacgc     180
cctacggggg aaagcagggg accttcgggc cactttcagc gaggaggaaa ggttggtagc     240
taataactgc cagctgtgac gttactcgca gaagaagcac cggctaactc cgggccttgc     300
gcgattggat gaacccaggt gggattagct agttggtgag gtaatggctc accaaggcga     360
cgatccctag ctggt                                                     375
```

<210> SEQ ID NO 35
<211> LENGTH: 386
<212> TYPE: DNA
<213> ORGANISM: Haemophilus influenzae
<220> FEATURE:
<221> NAME/KEY: misc_feature
<222> LOCATION: (1)..(386)
<223> OTHER INFORMATION: Cons_Heamophilus/1-1484

<400> SEQUENCE: 35

```
agagttttga atctggctca gattgaacgc tggcggcagg cctaacacat gcaagtcgag      60
cggcagcggg aaagtagctt ggtagcttgc acttttgcc ggcgagcggc ggacgggtga     120
gtaatgcctg gggatctgcc cagtcgagga gggggataac agttggaaac gactgctaat     180
accgcatacg ccctacgggg gaaaggaggg gaccttcggg ccactttcag cgaggaggaa     240
aggttggcgc ctaatacgtg tcaactgtga cgttactcgc agaagaagca ccggctaact     300
ccgggccttt cgcgattgga tgaacccagg tgggattagc tagttggtgg ggtaatggct     360
caccaaggcg acgatcccta gctggt                                         386
```

<210> SEQ ID NO 36
<211> LENGTH: 374
<212> TYPE: DNA
<213> ORGANISM: Edwardsiella tarda
<220> FEATURE:
<221> NAME/KEY: misc_feature
<222> LOCATION: (1)..(374)
<223> OTHER INFORMATION: Cons_E.tarda/1-1483

<400> SEQUENCE: 36

```
tggctcagat tgaacgctgg cggcaggctt aacacatgca agtcgagcgg tagcagggag      60
aaagcttgaa agcttgcttt ctccgctgac gagcggcgga cggtgagta atgtctgggg     120
atctgcctga tggagggagg gggataacta ctggaaacgg tagctaatac cgcataacgt     180
cgcaagacca aagtgggga ccttcgggcc actttcagta gggaggaagg tgtgaacgtt     240
aatagcgctc acaattgacg ttacctacag aagaagcacc ggctaactcc gggcctcatg     300
ccatcagatg aacccagatg ggattagcta gtaggtgggg taatggctca cctaggcgac     360
gatccctagc tggt                                                     374
```

<210> SEQ ID NO 37
<211> LENGTH: 337
<212> TYPE: DNA
<213> ORGANISM: Pseudoaltermonas sp.
<220> FEATURE:
<221> NAME/KEY: misc_feature
<222> LOCATION: (1)..(337)
<223> OTHER INFORMATION: Cons_Pseudoaltermonas/1-1453

<400> SEQUENCE: 37
```

```
cacatgcaag tcgagcggaa acgcagagta gcttggtagc ttgcttctct ggcgtcgagc    60
ggcggacggg tgagtaatgc ttgggaacat gccttgaggt ggtggggac aacagttgga    120 aacgactgct aataccgcat aatgtctacg gaccaaaggg ggcttcggct ctcgcacttt   180
cagtcaggag gaaaggttag tagttaatac ctgctagctg tgacgttact gacagaagaa    240
gcaccggcta actccggctc tcgcctttag attggcccaa gtgggattag ctagttggtg    300
aggtaatggc tcaccaaggc gacgatccct agctggt                              337
```

<210> SEQ ID NO 38
<211> LENGTH: 372
<212> TYPE: DNA
<213> ORGANISM: Marinomonas sp.
<220> FEATURE:
<221> NAME/KEY: misc_feature
<222> LOCATION: (1)..(372)
<223> OTHER INFORMATION: Cons_Marinomonas/1-1469

<400> SEQUENCE: 38

```
ctggctcaga ttgaacgctg gcggcaggct taacacatgc aagtcgagcg gtaacagggg    60
agcttgggag cttgctcctg ctgacgagcg gcggacgggt gagtaacgcg taggaatctg   120
cctagtagag gaggggaca acatgtggaa acgcatgcta ataccgcata cgccctgagg    180
gggaaaggag gggactttc ggagccactt tcagggtga ggaagggtga ttggttaata    240
cccaattatc ttgacgttag ccccagaaga agcaccggct aactctcgga gccttccgct    300
attagatgag cctgcgtgag attagctagt tggtagggta aaggcctacc aaggcgacga    360
tctctaactg gt                                                          372
```

<210> SEQ ID NO 39
<211> LENGTH: 364
<212> TYPE: DNA
<213> ORGANISM: Pseudomonas sp.
<220> FEATURE:
<221> NAME/KEY: misc_feature
<222> LOCATION: (1)..(364)
<223> OTHER INFORMATION: Cons_Pseudomonas/1-1475
<220> FEATURE:
<221> NAME/KEY: misc_feature
<222> LOCATION: (50)..(50)
<223> OTHER INFORMATION: n is a, c, g, or t
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (64)..(64)
<223> OTHER INFORMATION: n is a, c, g, or t
<220> FEATURE:
<221> NAME/KEY: misc_feature
<222> LOCATION: (78)..(78)
<223> OTHER INFORMATION: n is a, c, g, or t
<220> FEATURE:
<221> NAME/KEY: misc_feature
<222> LOCATION: (80)..(80)
<223> OTHER INFORMATION: n is a, c, g, or t
<220> FEATURE:
<221> NAME/KEY: misc_feature
<222> LOCATION: (135)..(135)
<223> OTHER INFORMATION: n is a, c, g, or t
<220> FEATURE:
<221> NAME/KEY: misc_feature
<222> LOCATION: (142)..(142)

<223> OTHER INFORMATION: n is a, c, g, or t
<220> FEATURE:
<221> NAME/KEY: misc_feature
<222> LOCATION: (150)..(150)
<223> OTHER INFORMATION: n is a, c, g, or t
<220> FEATURE:
<221> NAME/KEY: misc_feature
<222> LOCATION: (226)..(226)
<223> OTHER INFORMATION: n is a, c, g, or t
<220> FEATURE:
<221> NAME/KEY: misc_feature
<222> LOCATION: (229)..(229)
<223> OTHER INFORMATION: n is a, c, g, or t
<220> FEATURE:
<221> NAME/KEY: misc_feature
<222> LOCATION: (238)..(238)
<223> OTHER INFORMATION: n is a, c, g, or t

<400> SEQUENCE: 39

```
gctcagattg aacgctggcg gcaggcctaa cacatgcaag tcgagcggan ganggnagct    60
tggnagcttg ctcctggntn cgagcggcgg acgggtgagt aatgcctagg aatctgcctg   120
gtagtggtgg ggganaacgt tnggaaacgn acgctaatac cgcatacgtc ctacgggaga   180
aagcagggga ccttcgggcc actttaagtt gggaggaagg gcagtnacnt aatacgtngc   240
tgttttgacg ttaccgacag aataagcacc ggctaactct gggccttgcg ctatcagatg   300
agcctaggtc ggattagcta gttggtgagg taatggctca ccaaggcgac gatccgtaac   360
tggt                                                                364
```

<210> SEQ ID NO 40
<211> LENGTH: 392
<212> TYPE: DNA
<213> ORGANISM: Enterococcus sp.
<220> FEATURE:
<221> NAME/KEY: misc_feature
<222> LOCATION: (1)..(392)
<223> OTHER INFORMATION: Cons_Enterococcus/1-1493
<220> FEATURE:
<221> NAME/KEY: misc_feature
<222> LOCATION: (376)..(376)
<223> OTHER INFORMATION: n is a, c, g, or t

<400> SEQUENCE: 40

```
cctggctcag gacgaacgct ggcggcgtgc ctaatacatg caagtcgaac gcttttcctt    60
tcaccggagc ttgtcaccgg agcttgctcc accgaaagaa aaagagtggc gaacgggtga   120
gtaacacgtg ggtaacctgc ccatcagaag aagggggataa cacttggaaa caggtgctaa   180
taccgtataa cactatttc cgcatggaag aaagttgaaa ggcgcttttg tctgttgtta   240
gagaagaaca aggatgagag tagaacgttc atcccttgac ggtatctaac cagaaagcca   300
cggctaacta ctgcgtcact gatggatgga cccgcggtgc attagctagt tggtgaggta   360
acggctcacc aaggcnacga tgcatagccg ac                                 392
```

<210> SEQ ID NO 41
<211> LENGTH: 404
<212> TYPE: DNA
<213> ORGANISM: Vagococcus sp.
<220> FEATURE:
<221> NAME/KEY: misc_feature
<222> LOCATION: (1)..(404)
<223> OTHER INFORMATION: Cons_Vagococcus/1-1515
<220> FEATURE:
<221> NAME/KEY: misc_feature
<222> LOCATION: (26)..(27)
<223> OTHER INFORMATION: n is a, c, g, or t

<400> SEQUENCE: 41

```
agagtttgga tcatggctca ggacgnnaac gctggcggcg tgcctaatac atgcaagtcg      60
aacgctttga ttttcaccgg agcttgtcac cggagcttgc tccaccgaaa atcaaagagt     120
ggcggacggg tgagtaacac gtgggcaacc tgcccaacag aggaggggga taacacttgg     180
aaacaggtgc taataccgca taatttgttt tcccgcatgg gagaataata aaagacgctt     240
cggtctgttg ttagagaaga acaagtggga gagtaactgt tcccaccttg acggtatcta     300
accagaaagc cacggctaac tacgtgtcca ctgttggatg ggcccgcgct gcattagtta     360
gttggtgggg taatggccta ccaagaccgt gatgcatagc cgac                      404
```

<210> SEQ ID NO 42
<211> LENGTH: 383
<212> TYPE: DNA
<213> ORGANISM: Lysinibacillus sp.
<220> FEATURE:
<221> NAME/KEY: misc_feature
<222> LOCATION: (1)..(383)
<223> OTHER INFORMATION: Cons_Lysinibacillus/1-1449

<400> SEQUENCE: 42

```
catggctcag gacgaacgct ggcggcgtgc ctaatacatg caagtcgagc ggactttaga      60
aaagcttgta gaaaagcttg cttttctaaa gttagcggcg gacgggtgag taacacgtgg     120
gcaacctgcc ctatagttgt tggggataac tccgggaaac cggggctaat accgaataat     180
acattccttc tcctgttgga atgttgaaag atggtttacg ctctgttgta agggaagaac     240
aagtacagta gtaactggct gtaccttgac ggtaccttat tagaaagcca cggctaacta     300
ccgctatcgc tataggatgg gcccgcggcg cattagctag ttggtgaggt aacggctcac     360
caaggcgacg atgcgtagcc gac                                              383
```

<210> SEQ ID NO 43
<211> LENGTH: 382
<212> TYPE: DNA
<213> ORGANISM: Staphylococcus sp.
<220> FEATURE:
<221> NAME/KEY: misc_feature
<222> LOCATION: (1)..(382)
<223> OTHER INFORMATION: Cons_Staphylococcus/1-1498

<400> SEQUENCE: 43

```
cctggctcag gatgaacgct ggcggcgtgc ctaatacatg caagtcgagc gaacggataa      60
ggagcttgat aaggagcttg ctcctttgaa gttagcggcg gacgggtgag taacacgtgg     120
gtaacctacc tataagacta ctggaataac ttcgggaaac cggagctaat gccgataac     180 atttggaacc gcatggttct aaagtaaaag atggttttgc tctgttatta gggaagaaca     240
aatgtgtaag taactgtgca catcttgacg gtacctaatc agaaagccac ggctaactac     300
tgctatcact tatagatgga cccgcgccgt attagctagt tggtaaggta acggcttacc     360
aaggcaacga tacgtagccg ac                                               382
```

<210> SEQ ID NO 44
<211> LENGTH: 396
<212> TYPE: DNA
<213> ORGANISM: Streptococcus iniae
<220> FEATURE:
<221> NAME/KEY: misc_feature
<222> LOCATION: (1)..(396)
<223> OTHER INFORMATION: Cons_S.iniae/1-1506

<400> SEQUENCE: 44

```
aatagtttttt tttttggctc aggacgaacg ctgggcggcg tgcctaatac atgcaagtag    60
aacgctgagg attggtgctt gggattggtg cttgcactaa tccaaagagt tgcgaacggg   120
tgagtaacgc gtaggtaacc tacctcatag cggcggggga taactattgg aaacgatagc   180
taataccgca tgacactaga gtacacatgt acttaattta aaaggagcaa ttgctctgtt   240
gttagagaag aacggtaatg ggagtggaaa atccattacg tgacggtaac taaccagaaa   300
gggacggcta actactgctt cactatgaga tggacctgcg ttgtattagc tagttggtga   360
ggtaacggct caccaaggcg acgatacata gccgac                             396
```

```
<210> SEQ ID NO 45
<211> LENGTH: 385
<212> TYPE: DNA
<213> ORGANISM: Streptococcus parauberis
<220> FEATURE:
<221> NAME/KEY: misc_feature
<222> LOCATION: (1)..(385)
<223> OTHER INFORMATION: Cons_S.parauberis/1-1466

<400> SEQUENCE: 45
atcatggctc aggacgaacg ctggcggcgt gcctaataca tgcaagtaga acgctgaaga    60
ctggtgcttg agactggtgc ttgcactagt cagatgagtt gcgaacgggt gagtaacgcg   120
taggtaacct acctcatagc ggcggggat aactattgga acgatagct aataccgcat    180 gacaattaag tactcatgta ctaaatttaa aaggagcaat tgctctgttg ttagagaaga   240
acggtaatgg gagtggaaaa tccattacgt gacggtaact aaccagaaag ggacggctaa   300
ctactgcttc actatgagat ggacctgcgt tgtattagct agttggtgag gtaacggctc   360
accaaggcca cgatacatag ccgac                                         385
```

```
<210> SEQ ID NO 46
<211> LENGTH: 395
<212> TYPE: DNA
<213> ORGANISM: Lactococcus garviae
<220> FEATURE:
<221> NAME/KEY: misc_feature
<222> LOCATION: (1)..(395)
<223> OTHER INFORMATION: Cons_L.garviae/1-1501

<400> SEQUENCE: 46
gagtttgatc atggctcagg acgaacgctg gcggcgtgcc taatacatgc aagtcgagcg    60
atgattaaag atagcttgtt aaagatagct tgctattttt atgaagagcg gcgaacgggt   120
gagtaacgcg tgggaaatct gccgagtagc ggcggggac aacgtttgga aacgaacgct    180
aataccgcat aacaatgaga atcgcatgat tcttatttaa aagaagcaat tgctctgttg   240
ttagagaaga acgttaagta gagtggaaaa ttacttaagt gacggtatct aaccagaaag   300
ggacggctaa ctactgcttc actacttgat gatcccgcgt tgtattagct agttggtagt   360
gtaaaggact accaaggcga tgatacatag ccgac                              395
```

```
<210> SEQ ID NO 47
<211> LENGTH: 333
<212> TYPE: DNA
<213> ORGANISM: Leucobacterium sp.
<220> FEATURE:
<221> NAME/KEY: misc_feature
<222> LOCATION: (1)..(333)
<223> OTHER INFORMATION: Cons_Leucobacterium/1-1444
<220> FEATURE:
<221> NAME/KEY: misc_feature
<222> LOCATION: (2)..(2)
<223> OTHER INFORMATION: n is a, c, g, or t
```

<400> SEQUENCE: 47

```
cngccgtggc ggggtgctaa ccatgcaagt cgaacgctga agctcccagc ttgccagctt      60
gctgggggtg gatgagtggc gaacgggtga gtaacacgtg agtaacctgc cccgaactct     120
tctgggataa gcgctggaaa cggcgtctaa tactggatat gtcctatcac cgcatggtgt     180
gtaggtggaa agaattcttt tagtagggaa gaagcgaaag tgacggtacc tgcagaaaaa     240
gcaccggcta actactttgg ttcgggatgg actcgcggcc tatcagctag atggtgaggt     300
aatggctcac catggcgacg acgggtagcc ggc                                   333
```

<210> SEQ ID NO 48
<211> LENGTH: 333
<212> TYPE: DNA
<213> ORGANISM: Mycobacterium sp.
<220> FEATURE:
<221> NAME/KEY: misc_feature
<222> LOCATION: (1)..(333)
<223> OTHER INFORMATION: Cons_Micobacterium/1-1477
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (9)..(11)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (70)..(70)
<223> OTHER INFORMATION: n is a, c, g, or t
<220> FEATURE:
<221> NAME/KEY: misc_feature
<222> LOCATION: (156)..(156)
<223> OTHER INFORMATION: n is a, c, g, or t
<220> FEATURE:
<221> NAME/KEY: misc_feature
<222> LOCATION: (158)..(160)
<223> OTHER INFORMATION: n is a, c, g, or t
<220> FEATURE:
<221> NAME/KEY: misc_feature
<222> LOCATION: (164)..(164)
<223> OTHER INFORMATION: n is a, c, g, or t
<220> FEATURE:
<221> NAME/KEY: misc_feature
<222> LOCATION: (166)..(166)
<223> OTHER INFORMATION: n is a, c, g, or t
<220> FEATURE:
<221> NAME/KEY: misc_feature
<222> LOCATION: (175)..(177)
<223> OTHER INFORMATION: n is a, c, g, or t
<220> FEATURE:
<221> NAME/KEY: misc_feature
<222> LOCATION: (180)..(181)
<223> OTHER INFORMATION: n is a, c, g, or t
<220> FEATURE:
<221> NAME/KEY: misc_feature
<222> LOCATION: (216)..(216)
<223> OTHER INFORMATION: n is a, c, g, or t

<400> SEQUENCE: 48

```
agtgncngnn nggcgtctta ccatgcaagt cgaacgntga agcccagctt gccagcttgc      60
tgggtggatn agtggcgaac gggtgagtaa cacgtgagca acctgcccct gactcttctg     120
```

```
ggataagcgc tggaaacggc gtctaatact ggatangnnn cgtnancgca tggtnnncgn    180
ntggaaagat tttcttttag caggggaaga agcganagtg acggtacctg cagaaaaaag    240
caccggctaa ctactttcgg ttggggatgg gctcgcggcc tatcagcttg ttggtgaggt    300
aatggctcac caaggcgtcg acgggtagcc ggc                                 333
```

```
<210> SEQ ID NO 49
<211> LENGTH: 345
<212> TYPE: DNA
<213> ORGANISM: Artherobacterium sp.
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (1)..(345)
<223> OTHER INFORMATION: Cons_Artherobacterium/1-1467
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (24)..(25)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t
<220> FEATURE:
<221> NAME/KEY: misc_feature
<222> LOCATION: (125)..(125)
<223> OTHER INFORMATION: n is a, c, g, or t
<220> FEATURE:
<221> NAME/KEY: misc_feature
<222> LOCATION: (146)..(146)
<223> OTHER INFORMATION: n is a, c, g, or t
<220> FEATURE:
<221> NAME/KEY: misc_feature
<222> LOCATION: (176)..(182)
<223> OTHER INFORMATION: n is a, c, g, or t
<220> FEATURE:
<221> NAME/KEY: misc_feature
<222> LOCATION: (189)..(192)
<223> OTHER INFORMATION: n is a, c, g, or t
<220> FEATURE:
<221> NAME/KEY: misc_feature
<222> LOCATION: (194)..(194)
<223> OTHER INFORMATION: n is a, c, g, or t
<220> FEATURE:
<221> NAME/KEY: misc_feature
<222> LOCATION: (204)..(204)
<223> OTHER INFORMATION: n is a, c, g, or t
<220> FEATURE:
<221> NAME/KEY: misc_feature
<222> LOCATION: (228)..(229)
<223> OTHER INFORMATION: n is a, c, g, or t
<220> FEATURE:
<221> NAME/KEY: misc_feature
<222> LOCATION: (268)..(270)
<223> OTHER INFORMATION: n is a, c, g, or t
<220> FEATURE:
<221> NAME/KEY: misc_feature
<222> LOCATION: (275)..(276)
<223> OTHER INFORMATION: n is a, c, g, or t
<220> FEATURE:
<221> NAME/KEY: misc_feature
```

-continued

```
<222> LOCATION: (309)..(309)
<223> OTHER INFORMATION: n is a, c, g, or t
<220> FEATURE:
<221> NAME/KEY: misc_feature
<222> LOCATION: (319)..(320)
<223> OTHER INFORMATION: n is a, c, g, or t

<400> SEQUENCE: 49
nnntggctca ggatgaacgn tggnngngtg cttancacat gcaagtcgaa cgatgangcc      60
cagcttgcca gcttgctggg tggattagtg gcgaacgggt gagtaacacg tgagtaacct     120
gcccntgact cttctgggat aagccnggga aactgggtct aataccggat atgacnnnnn     180
nncgcatgnn nngnggtgga aagntttctt tcagtaggga agaagcgnna gtgacggtac     240
ctgcagaaga agcgccggct aactactnnn ggttnnggat ggactcgcgg cctatcagct     300
tgttggtgng gtaatggcnn accaaggcga cgacgggtag ccggc                     345

<210> SEQ ID NO 50
<211> LENGTH: 18
<212> TYPE: DNA
<213> ORGANISM: Artificial Sequence
<220> FEATURE:
<223> OTHER INFORMATION: Synthetic: oligonucleotide

<400> SEQUENCE: 50
atgccatcag atgaaccc                                                    18

<210> SEQ ID NO 51
<211> LENGTH: 18
<212> TYPE: DNA
<213> ORGANISM: Artificial Sequence
<220> FEATURE:
<223> OTHER INFORMATION: Synthetic: oligonucleotide

<400> SEQUENCE: 51
accagaaagg gacggcta                                                    18
```

GENETIC MARKER FOR DISCRIMINATING AND DETECTING CAUSATIVE BACTERIA OF FISH EDWARDSIELLOSIS AND STREPTOCOCCOSIS, AND METHOD FOR DISCRIMINATING AND DETECTING CAUSATIVE BACTERIA USING SAME

CROSS-REFERENCE TO RELATED APPLICATIONS

This application is a U.S. national phase under the provisions of 35 U.S.C. § 371 of International Patent Application No. PCT/KR2016/014215 filed Dec. 6, 2016, which in turn claims priority of Korean Patent Application No. 10-2015-0176870 filed Dec. 11, 2015. The disclosures of such international patent application and Korean priority patent application are hereby incorporated herein by reference in their respective entireties, for all purposes.

REFERENCE TO SEQUENCE LISTING SUBMITTED VIA EFS-WEB

This application includes an electronically submitted sequence listing in .txt format. The .txt file contains a sequence listing entitled "405_UpdatedSeqListing_ST25.txt" created on Apr. 8, 2020 and is 34,677 bytes in size. The sequence listing contained in this .txt file is part of the specification and is hereby incorporated by reference herein in its entirety.

TECHNICAL FIELD

The present invention relates to genetic markers for discrimination and detection of bacteria causing Edwardsiellosis and Streptococcosis in fish, and a method for discriminating and detecting the bacteria using the same. More specifically, the present invention relates to a method comprising: selecting a genetic marker containing a bacteria-specific single nucleotide polymorphism (SNP) from a DNA nucleotide sequence encoding the 16S rDNA gene of each of *Edwardsiella tarda, Streptococcus iniae, Streptococcus parauberis* and *Lactococcus garvieae*, which cause Edwardsiellosis and Streptococcosis in fish; amplifying the selected genetic marker; hybridizing a peptide nucleic acid (PNA) to the amplification product; controlling the temperature of hybridization product to obtain a temperature-dependent melting curve; and analyzing the melting curve to determine a melting temperature, thereby discriminating bacterial species or determining whether or not fish would be infected with the bacterial species.

BACKGROUND ART

Various methods for analyzing bacterial genes have been developed and used, including Sanger sequencing method, RAPD (random amplified polymorphic DNA) method, RFLP (restriction fragment length polymorphism) method, but these methods still entail a problem in that they are time-consuming and use complex procedures.

The detection of bacterial diseases in the aquaculture field relies on bacterial culture methods that are time-consuming. Such bacterial culture methods may pose problems associated with detection errors because of a lack of objectivity, and bacterial culture methods that use selective medium have disadvantages in that they can detect only single bacteria and cannot achieve detailed classification. In order to increase the accuracy of detection, a biological analysis method (API test) is used, but it uses a complex procedure and requires a long reaction time, and thus cannot achieve rapid detection. Particularly, since a database about bacteria associated with aquatic animal diseases is insufficient and the detection accuracy is low because of the insufficiency of database, this analysis method is not used in the actual aquatic field. When molecular detection products are developed, which overcome such problems and can achieve detection within a few hours, they make it possible to prevent damage caused by bacterial diseases in an early stage.

Many kinds of fish such as tilapia, yellowtail, Oncorhynchus mykiss, and flatfishes, which are aquacultured worldwide, are infected with *Edwardsiella tarda, Streptococcus iniae, Streptococcus parauberis* and *Lactococcus garvieae*, which cause Edwardsiellosis and Streptococcosis, and are perished. Particularly, *Streptococcus iniae* may infect humans to cause cellulitis, and 20 or more human cases infected with *Streptococcus iniae* in humans through fishes were reported in the USA, Canada, Hongkong, Taiwan and Singapore, and thus it is important to discriminate the infectivity and pathogenicity of these bacteria.

Accordingly, there is a need for a method which can easily analyze the genotype-specific pathogenicity of bacteria by selecting a genotype and a genetic marker of pathogenic bacteria detected in infected fish and using the genotype and the genetic marker. When markers as described above are developed, these markers make it possible to accurately detect and discriminate bacteria causing Streptococcosis and Edwardsiellosis, which frequently occur in aquacultured fish such as flatfishes. Furthermore, these markers make it possible to accurately identify the bacteria, by which individuals infected with the bacteria could be detected in an early stage and the abuse of antibiotics in fish could be prevented to thereby reduce the production cost of fish.

Under this technical background, the present inventors have made extensive efforts to develop a method for discriminating the species of bacteria causing Streptococcosis and Edwardsiellosis in fish and detecting individuals infected with the bacteria. As a result, the resent inventors have identified genetic markers for discrimination and/or detection of *Edwardsiella tarda, Streptococcus iniae, Streptococcus parauberis* and *Lactococcus garvieae*, which are bacteria causing fish diseases, and have found that when peptide nucleic acids and primer pairs, specific for the genetic markers, are used to obtain different fluorescence amplification and melting curves depending on bacterial species, the bacteria causing fish diseases can be discriminated in a simple, rapid and accurate manner, thereby completing the present invention.

DISCLOSURE OF INVENTION

Technical Problem

It is an object of the present invention to provide a genetic marker, a primer pair and a PNA probe for discrimination and detection of bacteria causing Edwardsiellosis or Streptococcosis.

Another object of the present invention is to provide a composition and a kit for discrimination and detection of bacteria causing Edwardsiellosis or Streptococcosis, in which the composition and the kit comprise the primer pair and the PNA probe.

Still another object of the present invention is to provide a method comprising amplifying a genetic marker region, containing a single nucleotide polymorphism (SNP) specific for bacteria causing Edwardsiellosis or Streptococcosis, by use of the primer pair, hybridizing the PNA probe to the amplified genetic marker region to obtain a $T_m$ value, thereby discriminating the species of the bacteria or detecting whether or not fish would be infected with the bacteria.

Technical Solution

To achieve the above object, the present invention provides a genetic marker for discrimination or detection of *Edwardsiella tarda*, which is represented by a single nucleotide polymorphism (SNP)-containing nucleotide sequence of SEQ ID NO: 8, which is a part of a DNA nucleotide sequence encoding the 16S rDNA gene of *Edwardsiella tarda*.

The present invention also provides a genetic marker for discrimination or detection of *Streptococcus* species (*Streptococcus iniae, Streptococcus parauberis* or *Lactococcus garvieae*), which is represented by a single nucleotide polymorphism (SNP)-containing nucleotide sequence of SEQ ID NO: 9, SEQ ID NO: 10 or SEQ ID NO: 11, which is a part of a DNA nucleotide sequence encoding the 16S rDNA gene of the *Streptococcus* species.

The present invention also provides a primer pair for discrimination or detection of *Edwardsiella tarda*, which is represented by nucleotide sequences of SEQ ID NOs: 1 and 2 and used for amplification of a genetic marker which is represented by a single nucleotide polymorphism (SNP)-containing nucleotide sequence of SEQ ID NO: 8, which is a part of a DNA nucleotide sequence encoding the 16S rDNA gene of *Edwardsiella tarda*.

The present invention also provides a primer pair for discrimination or detection of the *Streptococcus* species (*Streptococcus iniae, Streptococcus parauberis* or *Lactococcus garvieae*), which is represented by nucleotide sequences of SEQ ID NOs: 1 and 3 and used for amplification of a genetic marker which is represented by a single nucleotide polymorphism (SNP)-containing nucleotide sequence of SEQ ID NO: 9, SEQ ID NO: 10 or SEQ ID NO: 11, which is a part of a DNA nucleotide sequence encoding the 16S rDNA gene of the *Streptococcus* species.

The present invention also provides a PNA probe for discrimination or detection of *Edwardsiella tarda*, which is represented by a nucleotide sequence of SEQ ID NO: 4 and corresponds to the genetic marker of SEQ ID NO: 8 which contains a single nucleotide polymorphism (SNP) and is a part of the DNA nucleotide sequence encoding the 16S rDNA gene of *Edwardsiella tarda*.

The present invention also provides a PNA probe for discrimination or detection of *Streptococcus* species (*Streptococcus iniae, Streptococcus parauberis* or *Lactococcus garvieae*), which is represented by a nucleotide sequence of SEQ ID NO: 5, SEQ ID NO: 6 or SEQ ID NO: 7 and corresponds to the genetic marker of SEQ ID NO: 9, SEQ ID NO: 10 or SEQ ID NO: 11 which contains a single nucleotide polymorphism (SNP) and is a part of the DNA nucleotide sequence encoding the 16S rDNA gene of the *Streptococcus* species.

The present invention also provides a composition and a kit for discrimination and detection of *Edwardsiella tarda* or *Streptococcus* species, which comprises the above-described primer pair and the above-described PNA probe.

The present invention also provides a method for discrimination or detection of *Edwardsiella tarda* or *Streptococcus*, comprising the steps of: (a) extracting a target nucleic acid from a sample; (b) amplifying a genetic marker nucleotide sequence for *Edwardsiella tarda* or *Streptococcus* species, contained in the target nucleic acid, by use of the above-described primer pair, and hybridizing the above-described PNA probe to the amplified genetic marker nucleotide sequence; (c) obtaining a temperature-dependent melting curve while increasing the temperature of a PNA probe-hybridized product resulting from step (b); and (d) analyzing the melting curve obtained in step (c) to determine a melting temperature, thereby discriminating the bacterial species of *Edwardsiella tarda* or *Streptococcus* or detecting whether or not fish would be infected with the bacterial species.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

BEST MODE FOR CARRYING OUT THE INVENTION

Figure 1:
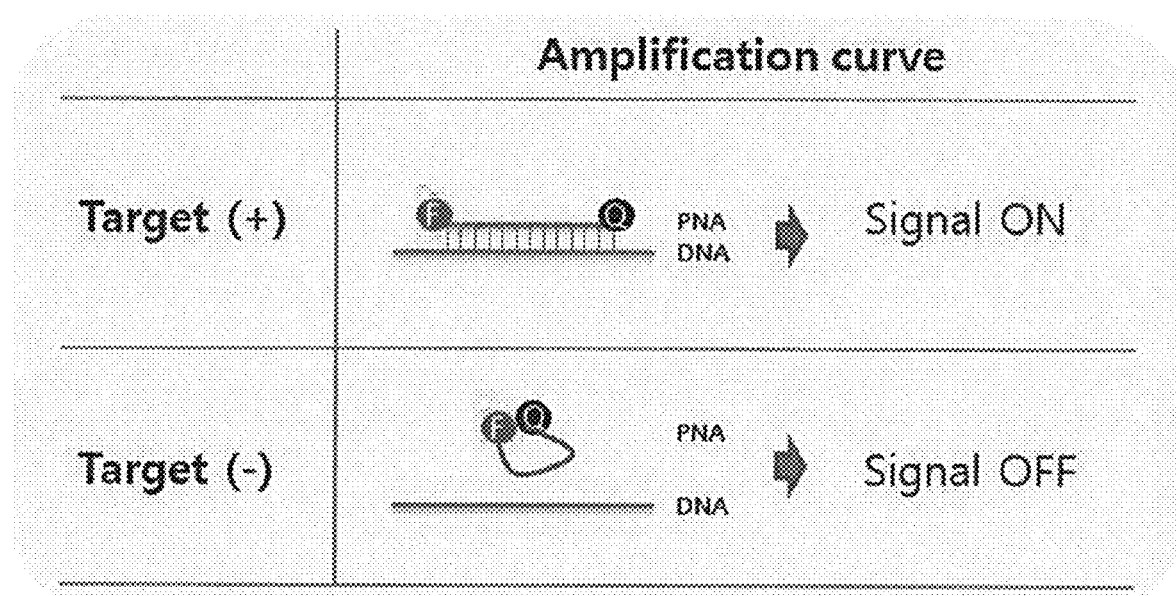
FIG. 1 is a conceptual view showing the technical characteristics of a step of obtaining an amplification curve for discrimination of bacterial species and detection of bacterial infection in individuals.
Figure 2:
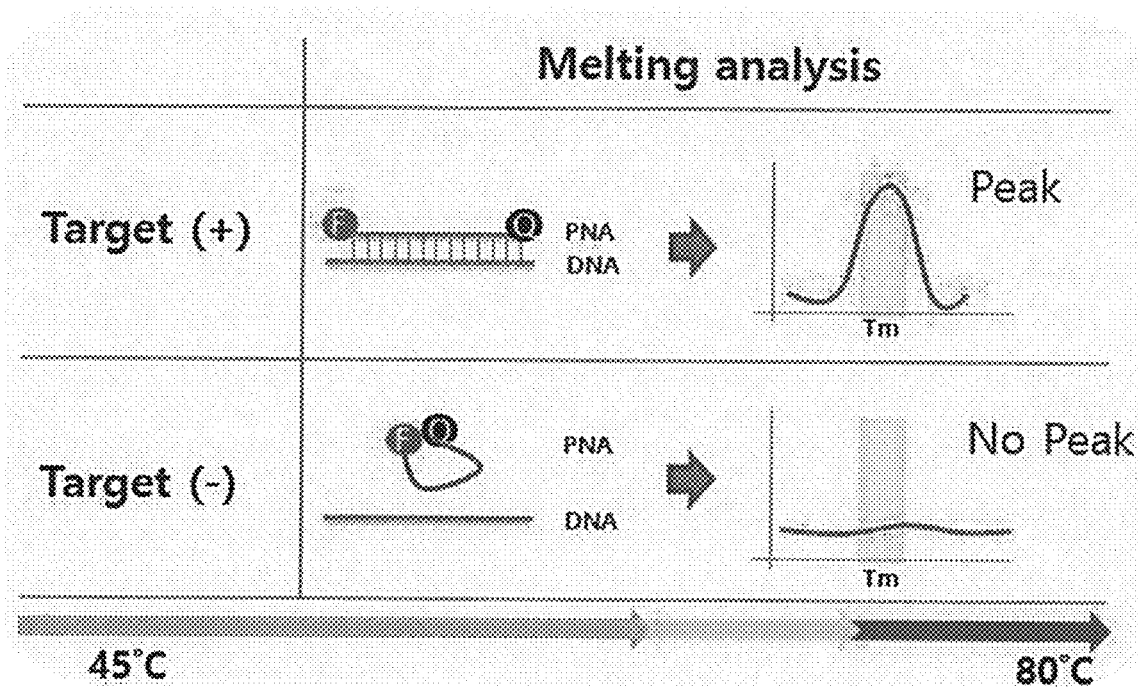
FIG. 2 is a schematic view showing a step of obtaining a melting curve by hybridization of a peptide nucleic acid in a method for discrimination of bacterial species and detection of bacterial infection in individuals.

Unless defined otherwise, all technical and scientific terms used herein have the same meaning as commonly understood by one of ordinary skill in the art to which the invention pertains. Generally, the nomenclature used herein and the experiment methods, which will be described below, are those well known and commonly employed in the art.

In one example of the present invention, in order to develop a method of discriminating bacterial species with genetic markers for discrimination and detection of Edwardsiellosis and Streptococcosis and detecting whether or not fish would be infected with the bacterial species, the 16S rDNA nucleotide sequences of the bacteria was obtained, and the consensus sequence of each bacterial species was constructed using CLC Genomic workbench 8.0.1, and then the genes were comparatively analyzed by clustal W alignment. From a DNA nucleotide sequence encoding the 16S rDNA gene of each of *Edwardsiella tarda* and *Streptococcus* species (*Streptococcus iniae, Streptococcus parauberis* and *Lactococcus garvieae*) selected through gene analysis, a genetic marker (region) containing a single nucleotide polymorphism (SNP) was selected as a target, and the species of bacteria causing Edwardsiellosis or Streptococcosis could be detected and discriminated using a primer pair and a PNA probe for discrimination of bacterial species, which correspond to the genetic marker.

More specifically, using primers having the nucleotide sequences of SEQ ID NOs: 1 to 3 constructed based on genetic markers having the nucleotide sequences of SEQ ID NOs: 8 to 11 obtained by comparatively analyzing the 16S rDNA nucleotide sequences of the bacteria, and PNA probes having the nucleotide sequences of SEQ ID NOs: 4 to 7, amplification and melting curves were obtained from bacterial DNAs by real-time polymerase chain reaction (PCR), and melting temperatures ($T_m$) were determined from the melting curves. As a result, as can be seen in the Example below, melting curves having different fluorescence depending on different bacterial species could be obtained.

Therefore, in one aspect, the present invention is directed to a genetic marker for discrimination or detection of *Edwardsiella tarda*, which is represented by a single nucleotide polymorphism (SNP)-containing nucleotide sequence of SEQ ID NO: 8, which is a part of a DNA nucleotide sequence encoding the 16S rDNA gene of *Edwardsiella tarda*.

In another aspect, the present invention is directed to a genetic marker for discrimination or detection of *Streptococcus* species (*Streptococcus iniae, Streptococcus parauberis* or *Lactococcus garvieae*), which is represented by a single nucleotide polymorphism (SNP)-containing nucleotide sequence of SEQ ID NO: 9, SEQ ID NO: 10 or SEQ ID NO: 11, which is a part of a DNA nucleotide sequence encoding the 16S rDNA gene of the *Streptococcus* species.

In still another aspect, the present invention is directed to a primer pair for discrimination or detection of *Edwardsiella tarda*, which is represented by nucleotide sequences of SEQ ID NOs: 1 and 2 and used for amplification of a genetic marker which is represented by a single nucleotide polymorphism (SNP)-containing nucleotide sequence of SEQ ID NO: 8, which is a part of a DNA nucleotide sequence encoding the 16S rDNA gene of *Edwardsiella tarda*.

In yet another aspect, the present invention is directed to a primer pair for discrimination or detection of the *Streptococcus* species (*Streptococcus iniae, Streptococcus parauberis* or *Lactococcus garvieae*), which is represented by nucleotide sequences of SEQ ID NOs: 1 and 3 and used for amplification of a genetic marker which is represented by a single nucleotide polymorphism (SNP)-containing nucleotide sequence of SEQ ID NO: 9, SEQ ID NO: 10 or SEQ ID NO: 11, which is a part of a DNA nucleotide sequence encoding the 16S rDNA gene of the *Streptococcus* species.

In a further aspect, the present invention is directed to a PNA probe for discrimination or detection of *Edwardsiella tarda*, which is represented by a nucleotide sequence of SEQ ID NO: 4 and corresponds to the genetic marker of SEQ ID NO: 8 which contains a single nucleotide polymorphism (SNP) and is a part of the DNA nucleotide sequence encoding the 16S rDNA gene of *Edwardsiella tarda*.

In a still further aspect, the present invention is directed to a PNA probe for discrimination or detection of *Streptococcus* species (*Streptococcus iniae, Streptococcus parauberis* or *Lactococcus garvieae*), which is represented by a nucleotide sequence of SEQ ID NO: 5, SEQ ID NO: 6 or SEQ ID NO: 7, and corresponds to the genetic marker of SEQ ID NO: 9, SEQ ID NO: 10 or SEQ ID NO: 11 which contains a single nucleotide polymorphism (SNP) and is a part of the DNA nucleotide sequence encoding the 16S rDNA gene of the *Streptococcus* species.

The PNA probe according to the present invention may have a reporter and a fluorescence quencher attached to both ends. The fluorescence quencher can quench the fluorescence of the reporter. The reporter may be one or more selected from the group consisting of FAM (6-carboxyfluorescein), Texas red, HEX (2',4',5',7',-tetrachloro-6-carboxy-4,7-dichlorofluorescein), JOE, Cy3, and Cy5. The quencher may be one or more selected from the group consisting of TAMRA (6-carboxytetramethyl-rhodamine), BHQ1, BHQ2 and Dabcyl, but is not limited thereto and preferably Dabcyl (FAM-labeled) can be used as the quencher.

Peptide nucleic acid (PNA) is a DNA analogue having nucleic acid connected by peptide bonds instead of phosphate bonds, and was first synthesized by Nielsen et al. in 1991. PNA is artificially synthesized by a chemical method, but not found in natural systems.

Peptide nucleic acid is one of substances that recognize genes, like LNA (locked nucleic acid) or MNA (morpholino nucleic acid). It is artificially synthesized and has a backbone consisting of polyamide. PNA is greatly excellent in affinity and selectivity and has a high stability for nucleolytic enzyme, and thus is not cleaved by an existing restriction enzyme. In addition, PNA advantageously has high thermal/chemical properties and stability, and thus its storage is easy and it is not easily broken down.

The PNA forms a duplex by its hybridization to a natural nucleic acid having a nucleotide sequence complementary thereto. When they have the same length, the PNA/DNA duplex is more stable than the DNA/DNA duplex and the PNA/RNA duplex is more stable than DNA/RNA duplex. Furthermore, since the PNA has a single base mismatch that makes the duplex unstable, the ability of the PNA to detect SNP (single nucleotide polymorphism) is better than that of natural nucleic acid.

Furthermore, PNA-DNA binding affinity is very high than DNA-DNA binding affinity, and thus there is a difference in melting point of about 10 to 15° C. even in the presence of one nucleotide mismatch. Using this difference in binding affinity, SNP (single-nucleotide polymorphism) and In/Del nucleotides changes can be detected.

Although the length of the PNA nucleotide sequence according to the present invention is not particularly limited, it may be constructed to have a length of 12 to 18-mer so as to contain the SNP of bacterial species. In the present invention, a PNA probe may be designed to have a desired $T_m$ value by adjusting the length of the PNA probe, and even in the case of PNA probes having the same length, the $T_m$ value may be adjusted by changing the nucleotide sequence. Furthermore, since a PNA probe has a binding affinity higher than a DNA probe, it has a higher $T_m$ value. Thus, the PNA probe can be designed to have a length shorter than a DNA probe, so that it can detect even adjacent SNPs. In a conventional HRM (High Resolution Melt) method, a difference in $T_m$ value from a target nucleic acid is as low as about 0.5° C., and thus an additional analytic program or a minute change or correction in temperature is required, and for this reason, it is difficult to perform analysis, when two or more SNPs appear. However, the PNA probe according to the present invention is not influenced by the PNA probe sequence and SNP, and thus makes it possible to perform analysis in a simple and convenient manner.

As described in the present invention, when the PNA probe comprises 14 nucleotides, it is preferable that the PNA probe contains one or more nucleotides corresponding to bacterial SNP sites in the middle of the sequences. Furthermore, the PNA probe may have, in the middle portion of the nucleotide sequence, a structural modification including a sequence corresponding to the SNP site of bacteria, thereby further increasing the difference in melting temperature ($T_m$) from a target nucleic acid to which it perfectly matches.

In a yet further aspect, the present invention is directed to a composition and a kit for discrimination and detection of *Edwardsiella tarda* or *Streptococcus* species, which comprises the above-described primer pair and the above-described PNA probe.

In the present invention, the *Streptococcus* species may be *Streptococcus iniae, Streptococcus parauberis*, or *Lactococcus garvieae*.

The kit of the present invention may optionally include reagents required for performing a target nucleic acid amplification reaction (e.g., PCR reaction), such as buffer, DNA polymerase cofactor, and deoxyribonucleotide-5-triphosphate. Alternatively, the kit of the present invention may also include various polynucleotide molecules, a reverse transcriptase, various buffers and reagents, and an antibody that inhibits the activities of a DNA polymerase. In addition, in the kit, the optimal amount of the reagent used in a specific reaction can be easily determined by those skilled in the art who have acquired the disclosure set forth herein. Typically, the kit of the invention may be manufactured as a separate package or compartment comprising the above mentioned ingredients.

When the kit is used, a single nucleotide mutation and a mutation caused by nucleotide deletion or insertion in a target nucleic acid can be effectively detected by analysis of a melting curve obtained using the PNA, thereby discriminating bacterial species.

In another further aspect, the present invention is directed to a method for discrimination or detection of *Edwardsiella tarda* or *Streptococcus* species, comprising the steps of: (a) extracting a target nucleic acid from a sample; (b) amplifying a genetic marker nucleotide sequence for *Edwardsiella tarda* or *Streptococcus*, contained in the target nucleic acid, by use of the above-described primer pair, and hybridizing the above-described PNA probe to the amplified genetic marker nucleotide sequence; (c) obtaining a temperature-dependent melting curve while increasing the temperature of a PNA probe-hybridized product resulting from step (b); and (d) analyzing the melting curve obtained in step (c) to determine a melting temperature, thereby discriminating the bacterial species of *Edwardsiella tarda* or *Streptococcus* or detecting whether or not fish would be infected with the bacterial species.

In the present invention, the *Streptococcus* species may be *Streptococcus iniae, Streptococcus parauberis*, or *Lactococcus garvieae*. In the present invention, the amplification may be performed by a real-time PCR (polymerase chain reaction) method.

In the present invention, when two or more target nucleic acids are used, the reporters attached to the PNA probes can be differ from each other depending on the kinds of target nucleic acid, and thus, the bacterial species of one or more *Edwardsiella tarda* and *Streptococcus* can be discriminated or detected by detecting two or more target nucleic acids simultaneously.

As used herein, the term "sample" is meant to include various samples. Preferably, a biosample is analyzed using the method of the present invention. More preferably, the sample may be either a sample that is mixed with the bacterial species of *Edwardsiella tarda* and/or *Streptococcus*, or a sample from an individual (for example, fish or the like) infected with the bacteria. Biosamples originated from plants, animals, humans, fungi, bacteria and virus can be analyzed. When a mammal- or human-originated sample is analyzed, it may be derived from specific tissues or organs. Representative examples of tissues include connective tissue, skin, muscle, or nerve tissue. Representative examples of organs include eyes, brain, lung, liver, spleen, bone marrow, thymus, heart, lymph, blood, bone, cartilage, pancreas, kidney, gallbladder, stomach, small intestine, testis, ovary, uterus, rectum, nervous system, and gland and internal blood vessels. A biosample to be analyzed includes any cell, tissue or fluid that is derived from a biological origin, or any other medium that can be well analyzed by the present invention. The biosample also includes a sample obtained from foods produced for consumption of humans and/or animals. In addition, the to-be-analyzed biosample includes a body fluid sample, which includes, but not limited to, blood, serum, plasma, lymph, breast milk, urine, feces, ocular fluid, saliva, semen, brain extracts (e.g., grinded brain), spinal fluid, appendix, spleen, and tonsil tissue extracts, but not limited thereto.

As used herein, the term "target nucleic acid", "synthetic DNA" or "artificially synthesized oligo" means a nucleic acid sequence (containing SNP) to be detected. The target nucleic acid comprises a specific region of the nucleic acid sequence of a "target gene" encoding a protein having physiological and biochemical functions, and is annealed or hybridized to the primer or the probe under annealing, hybridization, or amplification conditions.

As used herein, the term "hybridization" means that complementary single-stranded nucleic acids form a double-stranded nucleic acid. Hybridization can occur when the complementarity between two nucleic acid strands is perfect (perfect match) or when some mismatched residues exist. The degree of complementarity necessary for hybridization may vary depending on hybridization conditions, particularly may be controlled by temperature.

In the present invention, the melting curve analysis may be performed by a fluorescence melting curve analysis (FMCA) method.

The PNA probe comprising the reporter and the quencher according to the present invention generates a fluorescent signal after its hybridization to the target nucleic acid. As the temperature increases, the PNA probe is rapidly melted with the target nucleic acid at its suitable melting temperature, and thus the fluorescent signal is quenched. Through analysis of a high-resolution melting curve obtained from the fluorescent signal according to temperature changes, the presence or absence of a nucleotide modification (including SNP) may be detected. If the PNA probe perfectly matches with the nucleotide sequence of the target nucleic acid, it then shows an expected melting temperature ($T_m$) value, but if the PNA probe mismatches with a target nucleic acid in which a nucleotide mutation is present, it shows a melting temperature ($T_m$) value lower than an expected value.

As used herein, the term "nucleotide variation" refers to a change in a nucleotide sequence of a target nucleic acid (e.g., a substitution, deletion or insertion of one or more nucleotides, as well as a single nucleotide polymorphism (SNP)) relative to a reference sequence. The PNA probe of the present invention can analyze a change in a nucleotide sequence of a target nucleic acid such as SNP of the target nucleic acid or a substitution, deletion or insertion of nucleotides of the target nucleic acid through the melting curve analysis.

The PNA probe according to the present invention may have a reporter and a fluorescence quencher attached to both ends. The fluorescence quencher can quench the fluorescence of the reporter. The reporter may be one or more selected from the group consisting of FAM (6-carboxyfluorescein), Texas red, HEX (2',4',5',7',-tetrachloro-6-carboxy-4,7-dichlorofluorescein), JOE, Cy3, and Cy5. The quencher may be one or more selected from the group consisting of TAMRA (6-carboxytetramethyl-rhodamine), BHQ1, BHQ2 and Dabcyl, but is not limited thereto and preferably Dabcyl (FAM-labeled) can be used as the quencher.

The $T_m$ value also changes depending on the difference between the nucleotide sequence of the PNA probe and the nucleotide sequence of a DNA complementary thereto, and thus the development of applications based on this change is easily achieved. The PNA probe is analyzed using a hybridization method different from a hydrolysis method used for a TaqMan probe, and probes having functions similar to that of the PNA probe include molecular beacon probes and scorpion probes.

SNP (single-nucleotide polymorphism) analysis using the PNA probe can be sufficiently achieved using a forward/reverse primer set for PCR and a probe comprising nucleotides corresponding to a region containing an SNP. The PCR may be performed using a conventional method, and after completion of the PCR, a melting process is required. Whenever the melting temperature increases by 0.5° C., the intensity of fluorescence is measured to obtain the $T_m$ value. In particular, general real-time PCR systems are widely known and have an advantage in that purchase of an additional program such as a HRM (high-resolution melting) program or a minute temperature change is not required.

Melting curve analysis according to the present invention is a method of analyzing a double-chain nucleic acid formed of the target nucleic acid DNA or RNA and the probe. This method is called "melting curve analysis", because it is performed by, for example, $T_m$ analysis or the analysis of the melting curve of the double-strand nucleic acid. Using a probe complementary to a sequence containing a mutation (including SNP), a hybrid (double-chain DNA) of a target single-chain DNA and the probe is formed. Subsequently, the formed hybrid is heated, and the dissociation (melting) of the hybrid, which results from an increase in the temperature, is detected based on a change in a signal such as absorbance. Based on the results of the detection, the $T_m$ value is determined, whereby the presence or absence of a point mutation (including SNP) can be determined. The $T_m$ value increases as the homology of the formed hybrid increases, and the $T_m$ value decreases as the homology decreases. For this reason, the $T_m$ value of a hybrid formed of a point mutation-containing sequence to be detected and a probe complementary thereto is previously determined (a reference value for evaluation), and the $T_m$ value of a hybrid formed of the target single-chain DNA of a sample to be detected and the probe is measured (a measured value). If the measured value is approximately equal to the reference value, it can be determined that the probe matches, that is, a mutation (including SNP) is present in the target DNA. If the measured value is lower than the reference value, the probe mismatches, that is, no mutation is present in the target DNA.

The fluorescent melting curve analysis of the present invention is a method that analyzes a melting curve using a fluorescent material, and more specifically, may analyze the melting curve by using a probe containing a fluorescent material. The fluorescent material may be either a reporter or a quencher, and may preferably be an intercalating fluorescent material.

In the real-time polymerase chain reaction (PCR) method according to the present invention, a fluorescent substance is intercalated into a double-stranded DNA duplex during PCR, and the temperature is increased together with amplification to melt the DNA double strands to thereby reduce the amount of fluorescent substance present between the DNA double strands. The resulting melting curve pattern, particularly the temperature ($T_m$) at which the DNA is melted (denatured), may be analyzed, thereby determining the difference in nucleotide sequence between a normal control group and a mutation sequence (including SNP).

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1: Construction of Genetic Markers for Discrimination and Detection of Bacteria Causing Edwardsiellosis and Streptococcosis in Fish, and Primer Pairs and PNA Probes Specific for the Bacteria In order to discriminate the genotypes of bacterial 16S rDNA genes in 461 bacteria strains isolated from Korean aquacultured flatfishes, among bacteria causing fish infections, 16S rDNA nucleotide sequences were obtained through Sanger sequencing, and consensus sequences corresponding to bacterial species were constructed using CLC Genomic workbench 8.0.1 and comparatively analyzed by clustal W alignment. Through genotype analysis, nucleotide sequences (SEQ ID NOs: 8 to SEQ ID NOs: 11) specific for three *Streptococcus* species (*Streptococcus iniae*, *Streptococcus parauberis*, *Lactococcus garviae*) and *Edwardsiella*

*tarda* were selected as genetic markers for discrimination and detection of bacterial species.

More specifically, the single nucleotide polymorphism (SNP)-containing genetic markers of the DNA nucleotide sequences encoding the 16S rDNA genes were constructed such that a genetic marker site for the *Streptococcus iniae* 16S rDNA gene would comprise a sequence of 5'-CATGT-GTACTCTAG-3' (*Streptococcus iniae* 16S rDNA marker: SEQ ID NO: 9), a genetic marker site for the *Streptococcus parauberis* 16S rDNA gene would comprise a sequence of 5'-CAAGCACCAGTCTT-3' (*Streptococcus parauberis* 16S rDNA marker: SEQ ID NO: 10), a genetic marker site for the *Lactococcus garvieae* 16S rDNA gene would comprise a sequence of 5'-CTACTCGGCAGATT-3' (*Lactococcus garvieae* 16S rDNA marker: SEQ ID NO: 11), and a genetic marker site for the *Edwardsiella tarda* 16S rDNA gene would comprise a sequence of 5'-TGGTCTTGCGACGT-3' (*Edwardsiella tarda* 16S rDNA marker: SEQ ID NO: 8).

In addition, in order to detect the presence or absence of three *Streptococcus* species (*Streptococcus iniae*, *Streptococcus parauberis* and *Lactococcus garviae*) or *Edwardsiella tarda*, primers capable of amplifying specific sites of 16S rDNA were constructed as a reverse primer (SEQ ID NO: 2) specific for *Edwardsiella tarda* and a universal reverse primer (SEQ ID NO: 3) specific for *Streptococcus iniae*, *Streptococcus parauberis* and *Lactococcus garvieae*.

Herein, the primer (SEQ ID NO: 2) capable of amplifying the *Edwardsiella tarda* 16S rDNA gene was constructed to be complementary to a sequence of 5'-ATGCCATCAGAT-GAACCC-3' (SEQ ID NO: 50), and the universal reverse primer (SEQ ID NO: 3) capable of amplifying specific regions of 16S rDNA of three *Streptococcus* species (*Streptococcus iniae*, *Streptococcus parauberis* and *Lactococcus garviae*) was constructed to be complementary to a sequence of 5'-ACCAGAAAGGGACGGCTA-3' (SEQ ID NO: 51).

In addition, as a forward primer, a universal forward primer 27F (SEQ ID NO: 1) targeting bacterial 16S rDNA was used (Lane et al., 1991).

The PNA probes used in the present invention were designed using a PNA probe designer (Applied Biosystems, USA), and were constructed to comprise a bacteria-specific nucleotide sequence, a reporter and a quencher. Herein, the PNA probes were labeled with FAM, HEX, TexasRed and Cy5, respectively, such that they would not comprise the same fluorescence.

All the PNA probes (FAM-labeled, Dabcyl) used in the present invention were synthesized using a HPLC purification method by Panagene (Korea), and the purities of all the synthesized probes were analyzed by mass spectrometry (the unnecessary secondary structures of the probes were avoided for effective binding to target nucleic acids).

Figure 4:
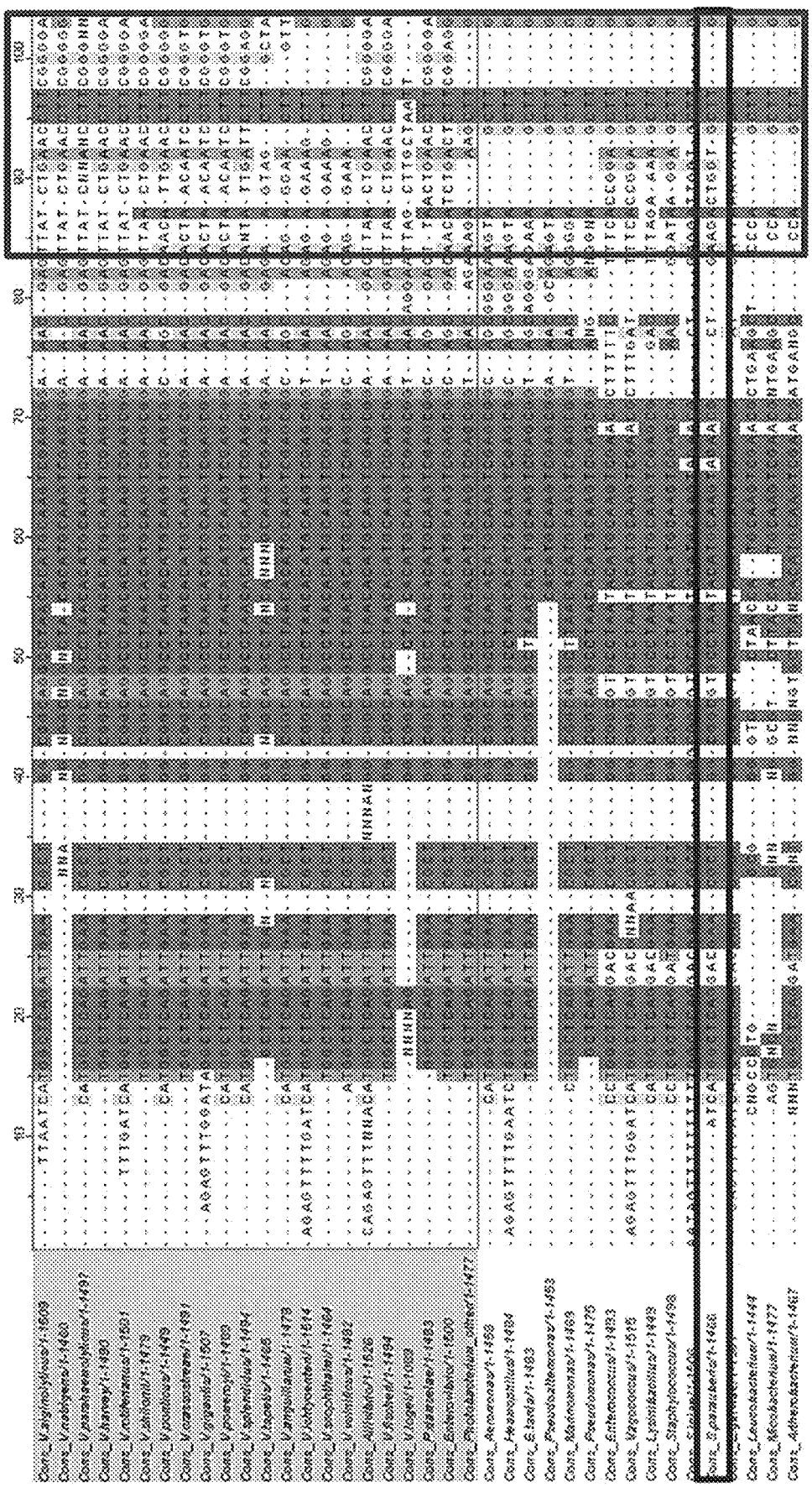
FIG. 4 is a gene position view illustrating nucleotide mutation sites included in 16S rDNA gene-specific peptide nucleic acids for discrimination and detection of *Streptococcus parauberis* (see corresponding segments in SEQ ID NOS: 12-49).
Figure 5:
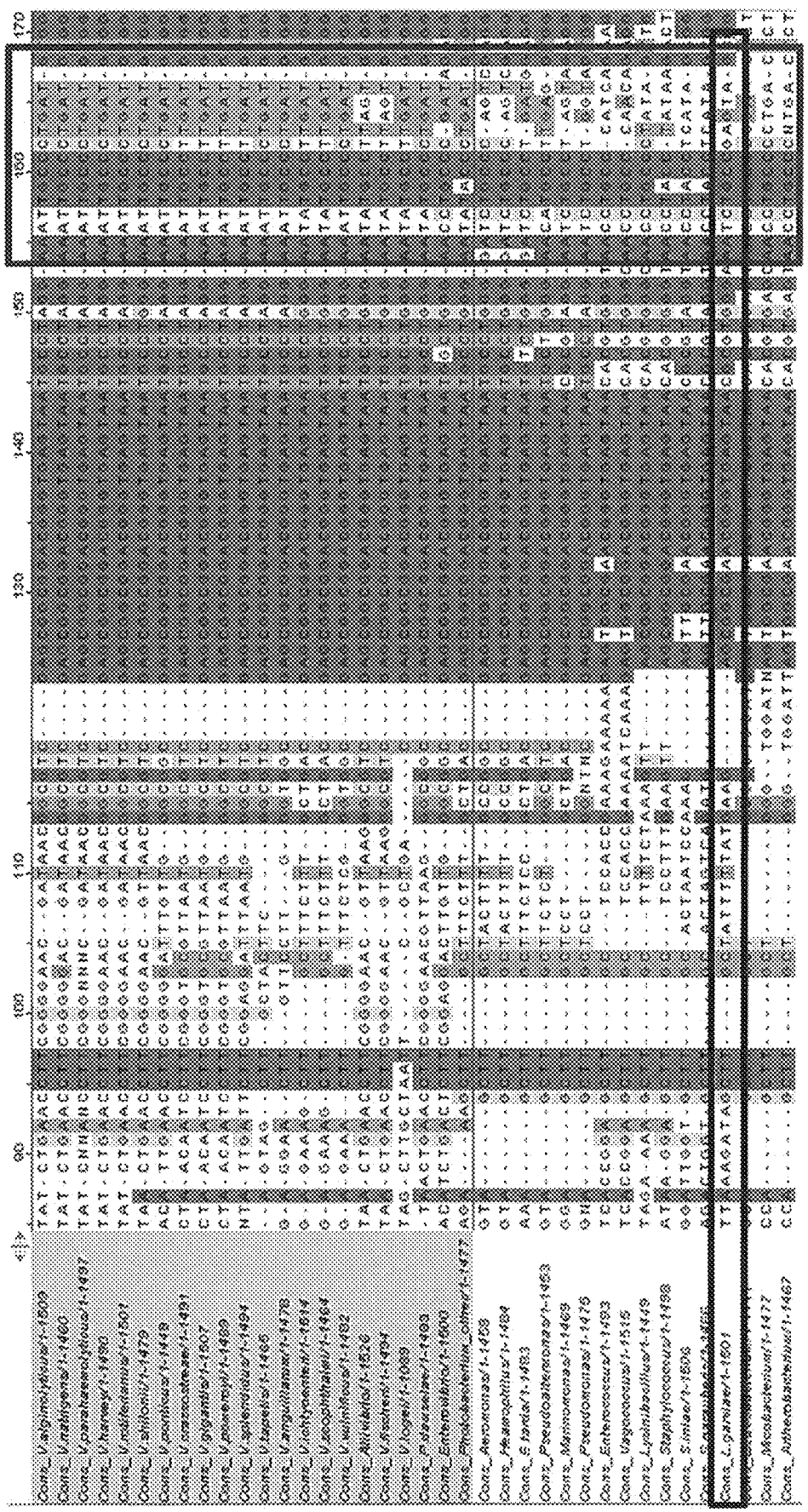
FIG. 5 is a gene position view illustrating nucleotide mutation sites included in 16S rDNA gene-specific peptide nucleic acids for discrimination and detection of *Lactococcus garvieae* (see corresponding segments in SEQ ID NOS: 12-49).
Figure 6:
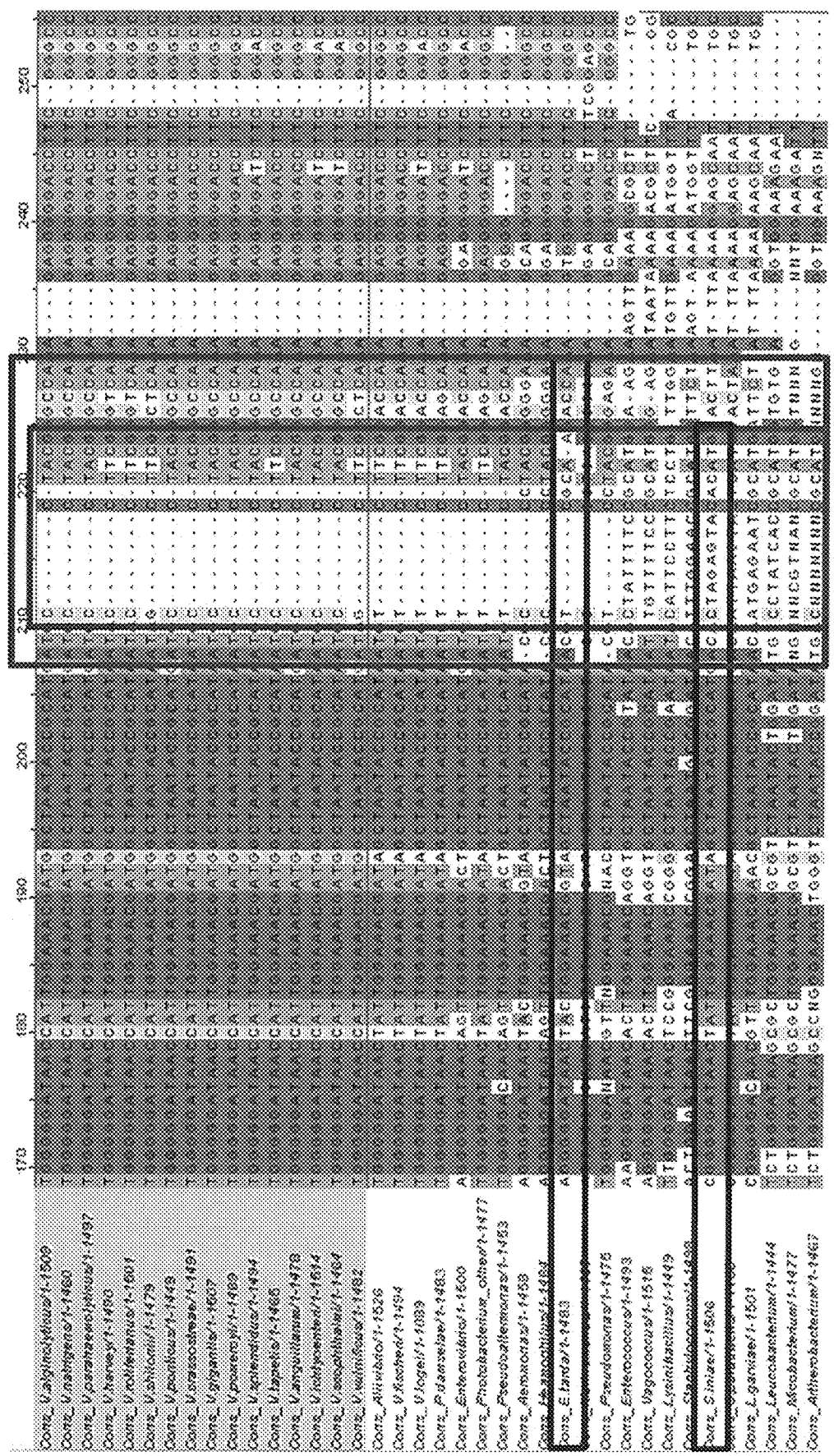
FIG. 6 is a gene position view illustrating nucleotide mutation sites included in 16S rDNA gene-specific peptide nucleic acids for discrimination and detection of *Edwardsiella tarda* and *Streptococcus iniae* (see corresponding segments in SEQ ID NOS: 12-49).
Figure 7:
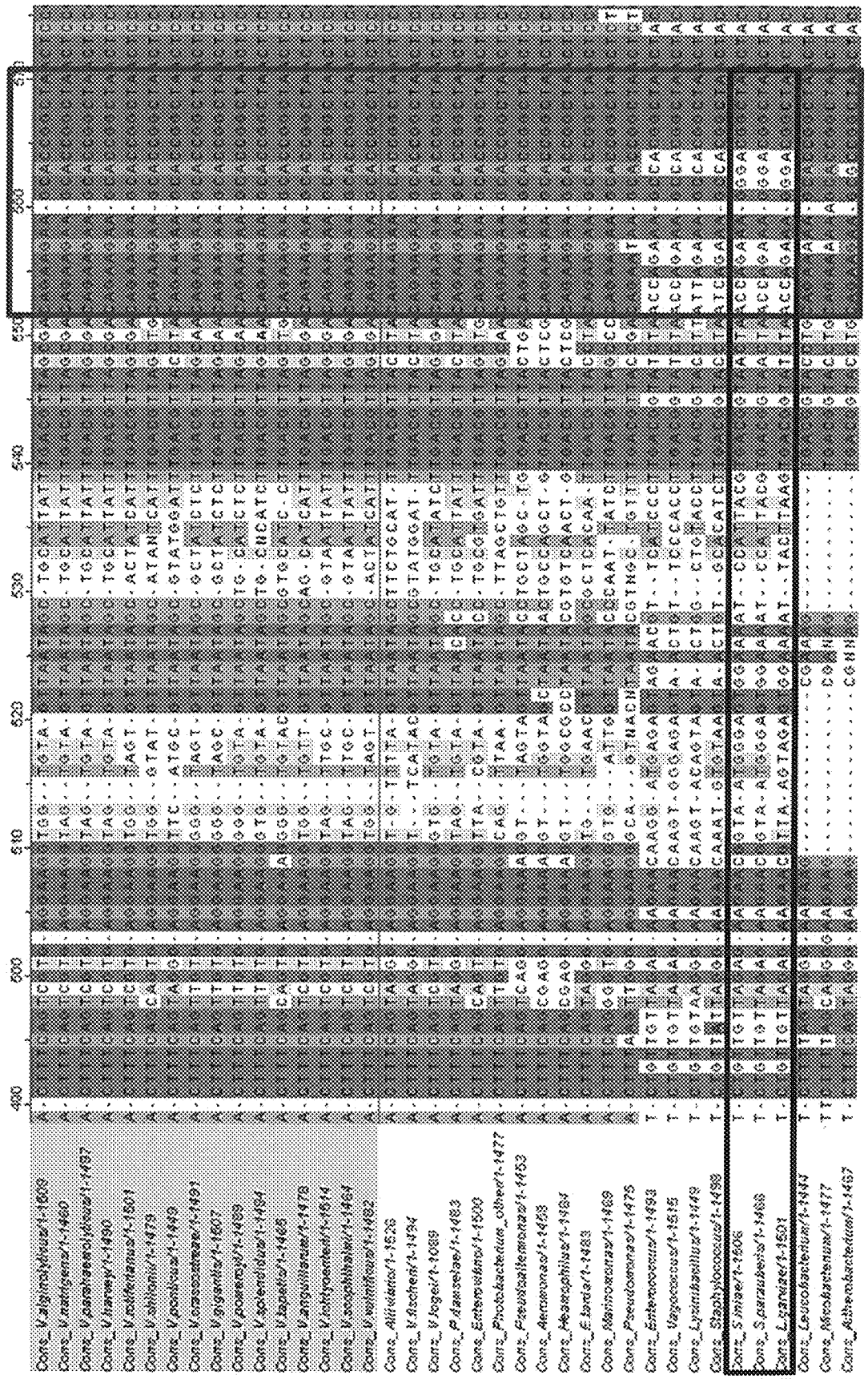
FIG. 7 is a gene position view illustrating nucleotide mutation sites included in 16S rDNA gene-specific primers for PCR amplification of three *Streptococcus* species (*Streptococcus iniae, Streptococcus parauberis*, and *Lactococcus garvieae*) (see corresponding segments in SEQ ID NOS: 12-49).
Figure 8:
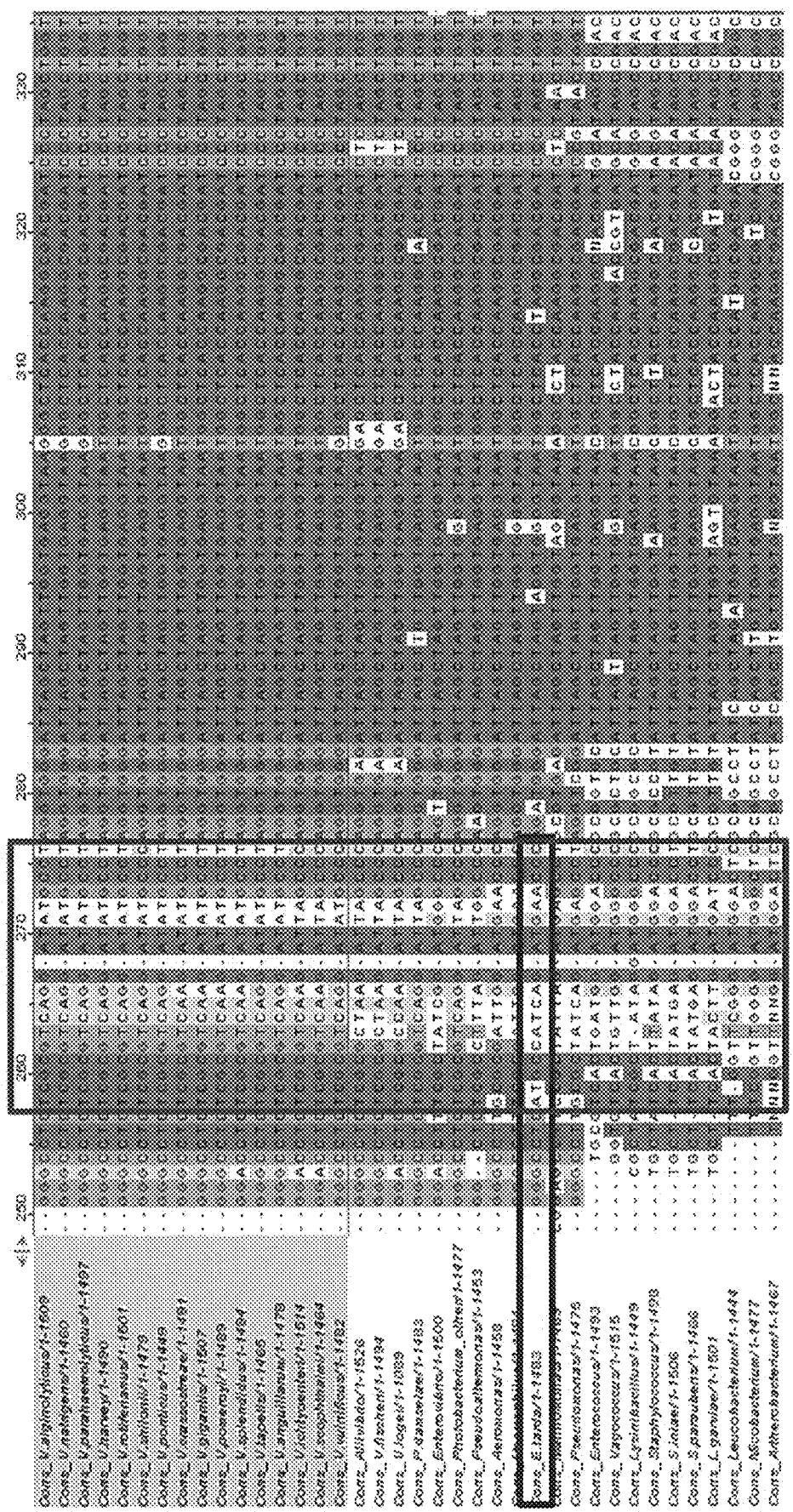
FIG. 8 is a gene position view showing an example of a nucleotide mutation site included in 16S rDNA gene-specific primers for PCR amplification of *Edwardsiella tarda* (see corresponding segments in SEQ ID NOS: 12-49).
Figure 9:
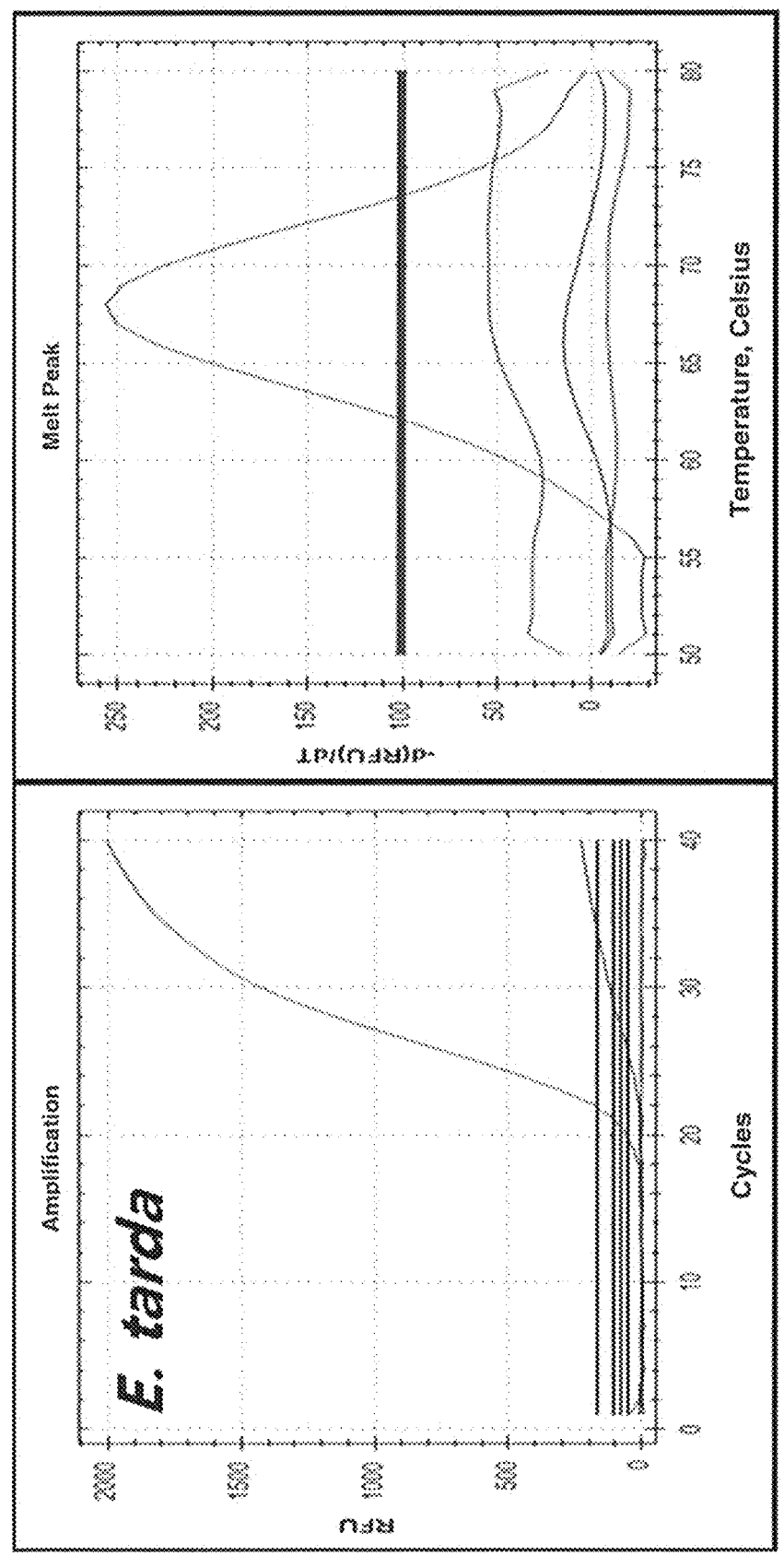
FIG. 9 shows amplification curve and melting curve graphs of *Edwardsiella tarda* (*E. tarda*), obtained using peptide nucleic acid probes and a primer pair for discrimination and detection of bacterial species.
Figure 10:
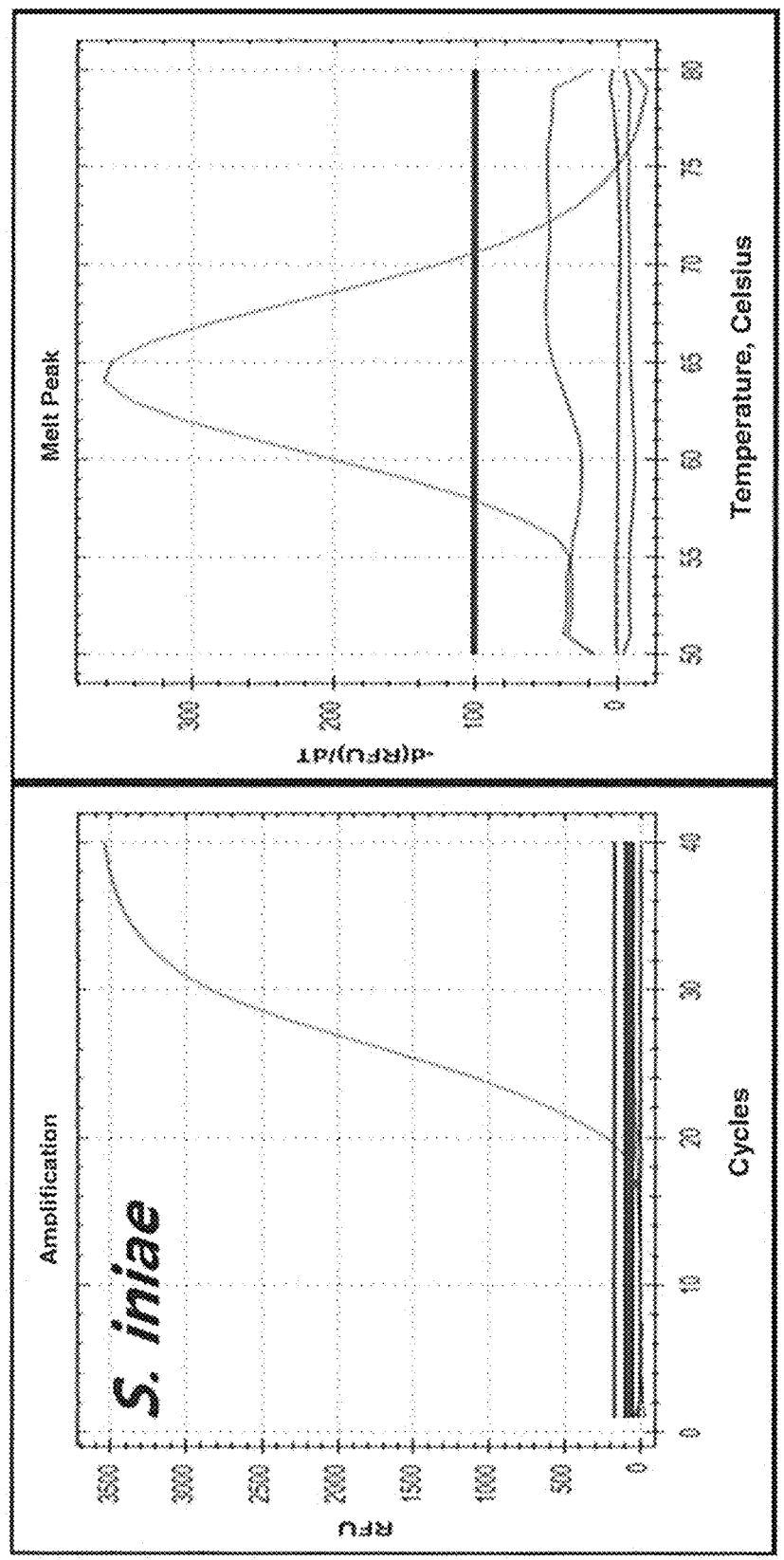
FIG. 10 shows amplification curve and melting curve graphs of *Streptococcus iniae* (*S. iniae*), obtained using peptide nucleic acid probes and a primer pair for discrimination and detection of bacterial species.
Figure 11:
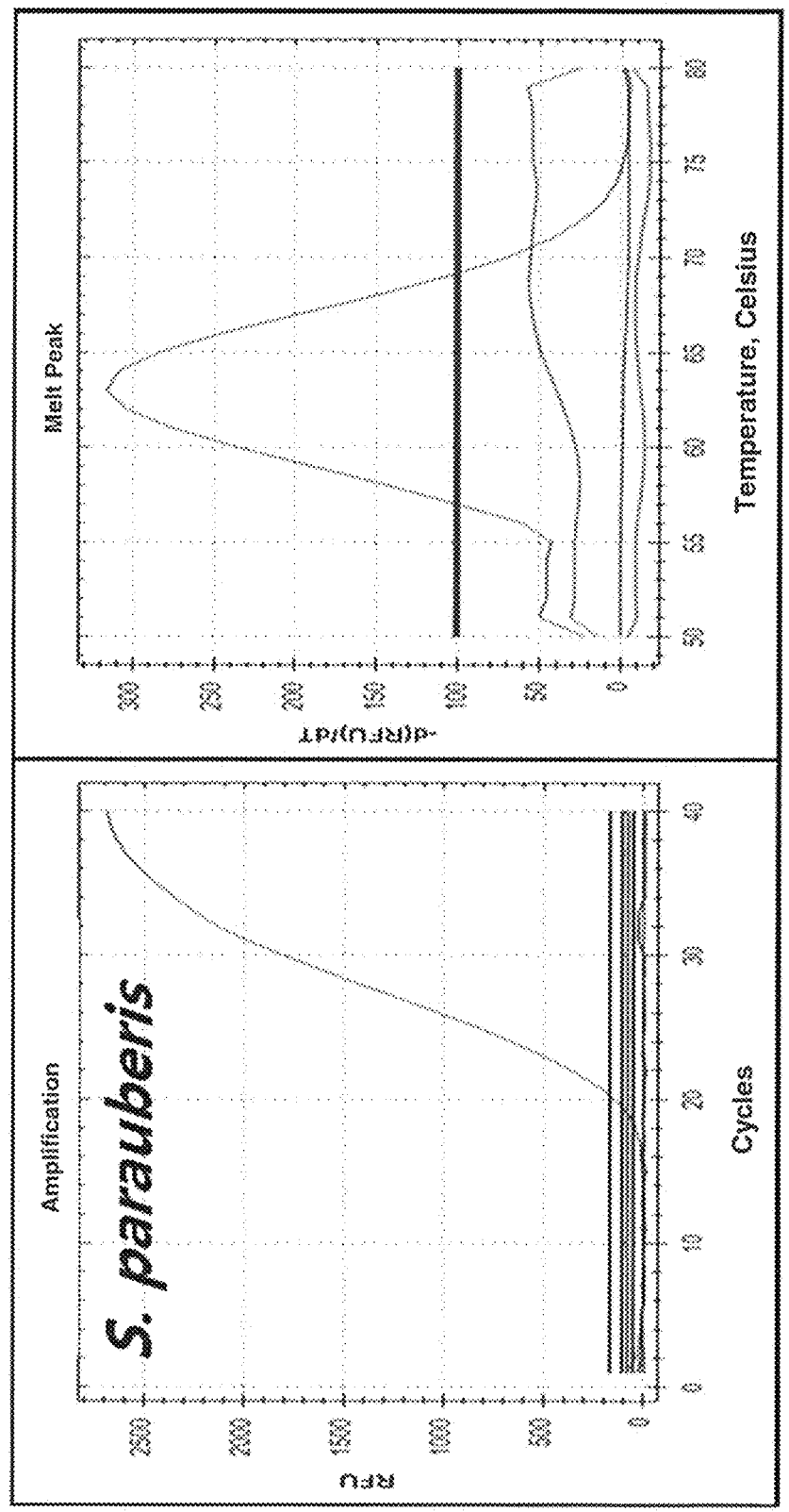
FIG. 11 shows amplification curve and melting curve graphs of *Streptococcus parauberis* (*S. parauberis*), obtained using peptide nucleic acid probes and a primer pair for discrimination and detection of bacterial species.
Figure 12:
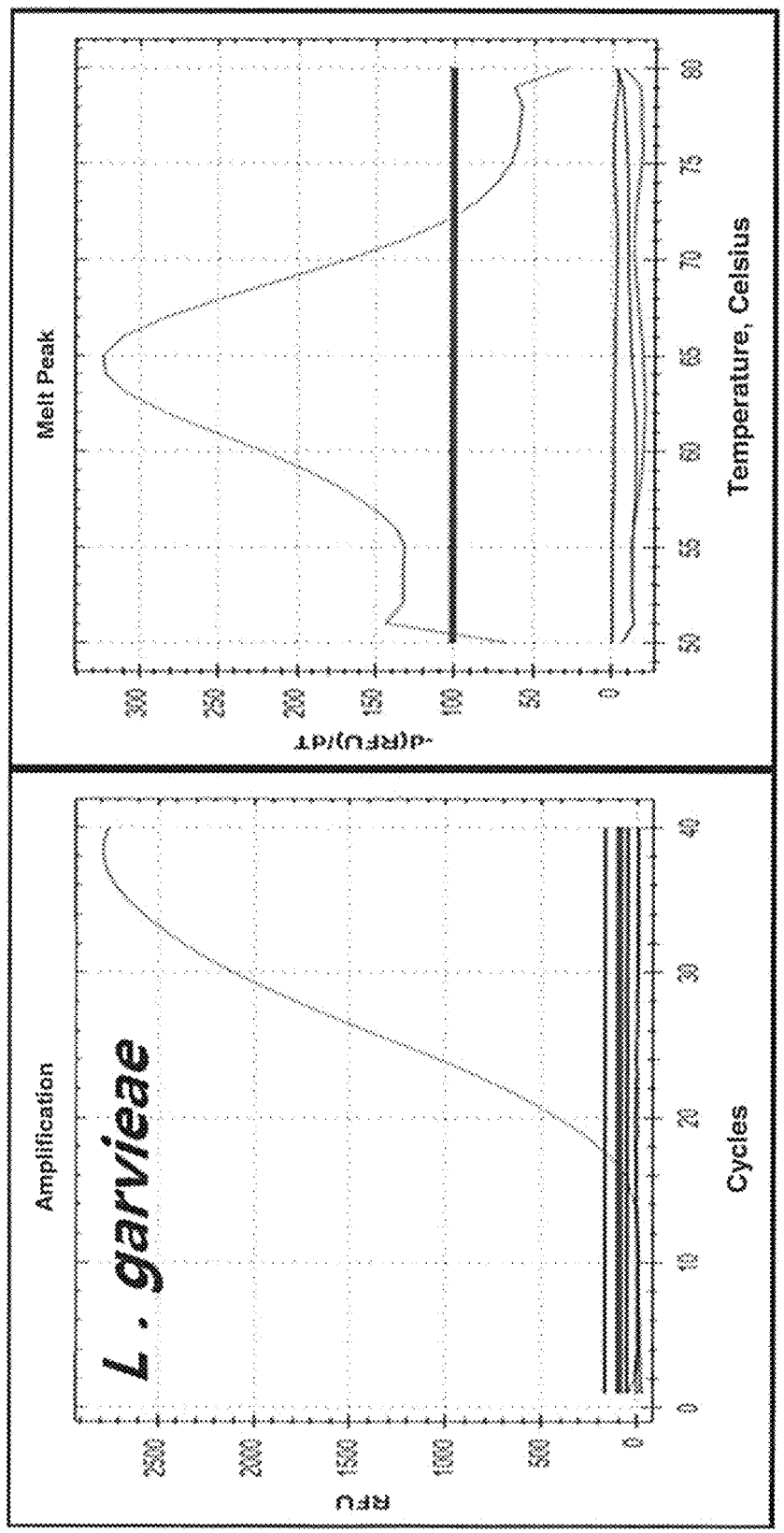
FIG. 12 shows amplification curve and melting curve graphs of *Lactococcus garvieae*, obtained using a peptide nucleic acid probe and a primer pair for discrimination and detection of bacterial species.

FIGS. 4 to 6 show nucleotide sequence views illustrating the nucleotide sequences of a portion and SNP of the 16S rDNA gene of each of the four bacterial species (*Streptococcus iniae*, *Streptococcus parauberis*, *Lactococcus garvieae*, and *Edwardsiella tarda*) according to the present invention and peptide nucleic acids (PNA) derived therefrom, and FIGS. 7 to 8 are gene position views illustrating regions including primer positions on the bacterial 16S rDNA genes. In FIGS. 4 to 8, the nucleotide sequence of each of the PNA probes is indicated by green color, and the nucleotide sequence specific for each bacterial species is indicated by black color.

As a result, the PNA and primer nucleotide sequences according to the present invention are shown in Table 1 below.

TABLE 1

| Classification | Name | SEQ ID NOs: | Sequences (5'-> 3') | Modifications | Targets |
|---|---|---|---|---|---|
| Primer | Universal forward Primer (27F) | SEQ ID NO: 1 | AGAGTTTGATCCTGG CTCAG | — | Bacterial 16S rDNA |
| | Reverse primer | SEQ ID NO: 2 | GGGTTCATCTGATGG CAT | — | *Edwardsiella tarda* |
| | Universal reverse primer | SEQ ID NO: 3 | TAGCCGTCCCTTTCTG GT | — | *Streptococcus iniae*, *Streptococcus parauberis*, *Lactococcus garvieae* |
| PNA probe | PNA 1 | SEQ ID NO: 4 | ACGTCGCAAGACCA | Dabsyl, FAM | *Edwardsiella tarda* |
| | PNA 2 | SEQ ID NO: 5 | CTAGAGTACACATG | Dabsyl, TexasRed | *Streptococcus iniae* |
| | PNA 3 | SEQ ID NO: 6 | AAGACTGGTGCTTG | Dabsyl, HEX | *Streptococcus parauberis* |
| | PNA 4 | SEQ ID NO: 7 | AATCTGCCGAGTAG | Dabsyl, Cy5 | *Lactococcus garvieae* |
| 16S rDNA marker | *Edwardsiella tarda*_16S rDNA marker | SEQ ID NO: 8 | TGGTCTTGCGACGT | — | *Edwardsiella tarda* |
| | *Streptococcus iniae*_16S rDNA marker | SEQ ID NO: 9 | CATGTGTACTCTAG | — | *Streptococcus iniae* |
| | *Streptococcus parauberis*_16S rDNA marker | SEQ ID NO: 10 | CAAGCACCAGTCTT | — | *Streptococcus parauberis* |
| | *Lactococcus garvieae*_16S rDNA marker | SEQ ID NO: 11 | CTACTCGGCAGATT | — | *Lactococcus garvieae* |

Example 2: Discrimination of Four Bacterial Genes by Real-Time Polymerase Chain Reaction (PCR) and Melting Curve Analysis Using the bacteria-specific genetic markers, PNA probes and primers of Example 1, amplification curves and melting curves for four bacterial DNA samples were obtained and analyzed to discriminate bacterial species.

PCR was performed using CFX96™ Real-Time system (Bio-Rad Laboratories Inc., USA) under asymmetric PCR conditions in order to produce single-stranded target nucleic acids. The asymmetric PCR conditions were as follows. 1 µM of a mixture of four PNA probes and 10 ng of bacterial DNA were added to 2×PNA qPCR PCR MasterMix (Seasun Biomaterials, Korea), 0.1 µM forward primer and 1 µM reverse primer to a total volume of 20 µL, and then real-time PCR was performed.

Figure 3:
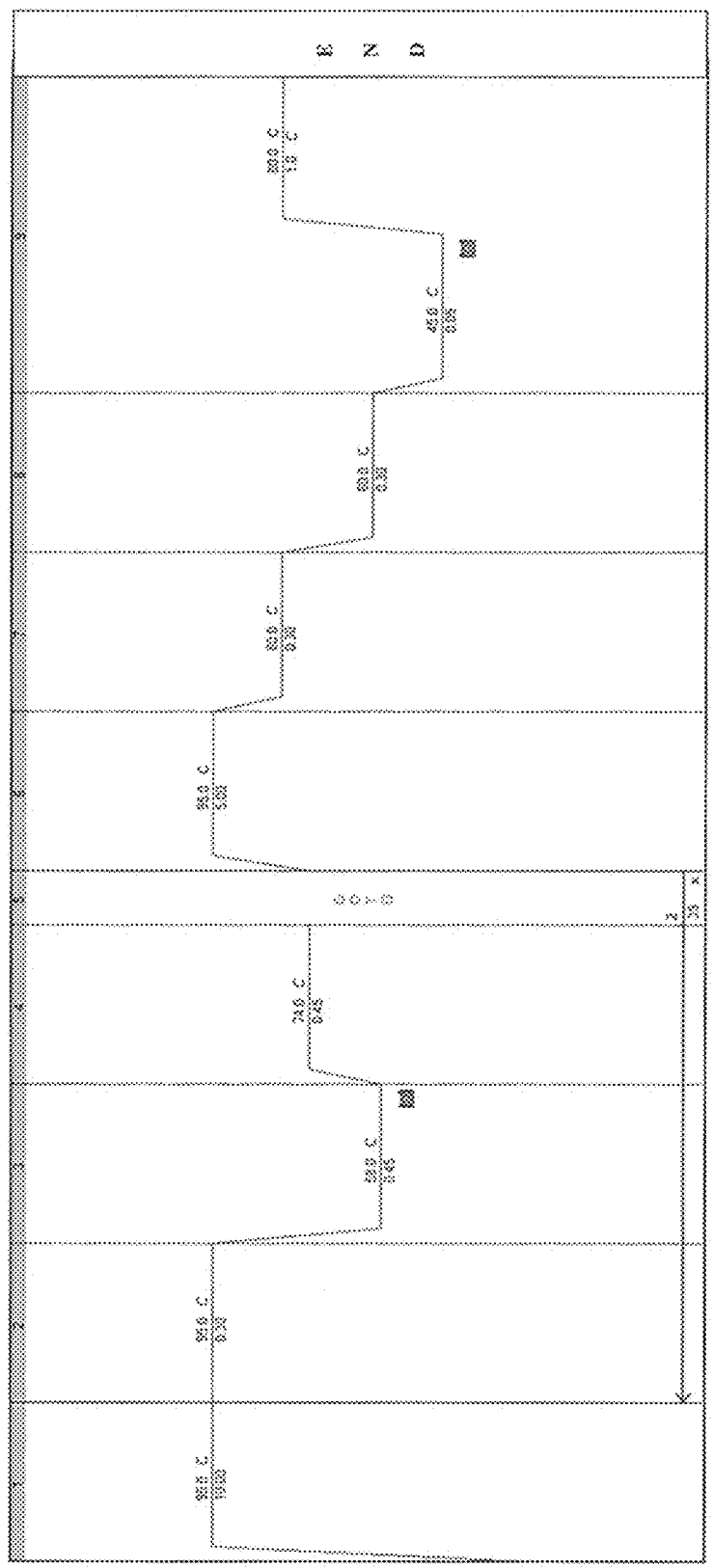
FIG. 3 shows real-time polymerase chain reaction (PCR) conditions for discrimination of bacterial species and detection of bacterial infection in individuals.

FIG. 3 shows real-time PCR reaction conditions for discrimination and detection of bacterial species. Specifically, FIG. 3 graphically shows a process of amplifying and hybridizing the genetic marker region of bacterial DNA and increasing the temperature of the hybridized product. Herein, the real-time PCR process was performed under the following conditions, and fluorescence was measured in real time: denaturation at 95° C. for 10 min, and then 40 cycles, each consisting of 95° C. for 30 sec, 58° C. for 45 sec, and 74° C. for 45 sec. Fluorescence was measured in real time. Melting curve analysis was performed under the following conditions while fluorescence was measured: denaturation at 95° C. for 5 min, and then maintenance at 80° C. for 30 sec and 60° C. for 30 sec, and temperature rising from 45° C. to 80° C. at a rate of 1° C.

Figure 13:
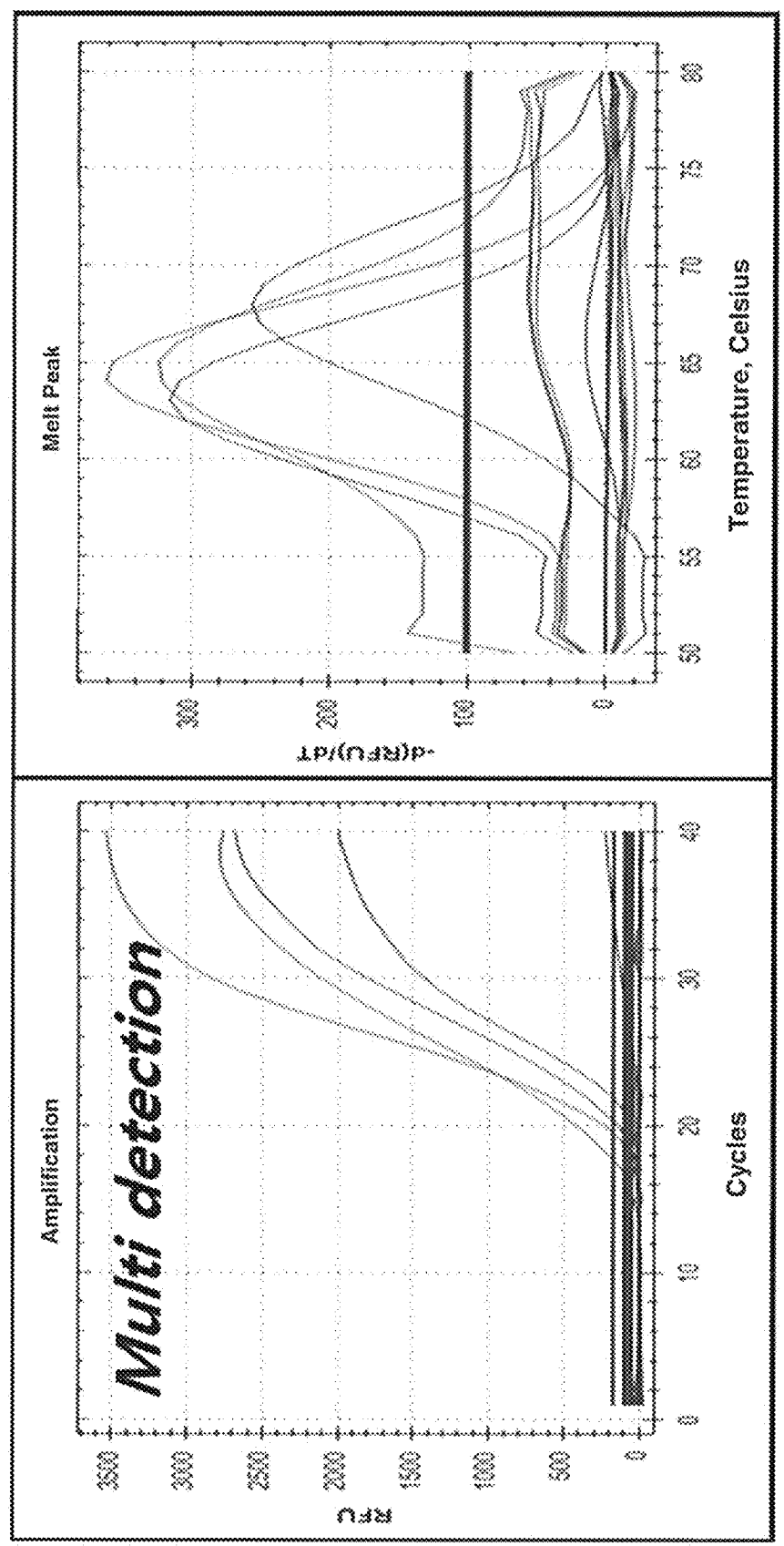
FIG. 13 shows amplification curve and melting curve graphs for a host (fish) infected simultaneously with four bacterial species (*Streptococcus iniae, Streptococcus parauberis, Lactococcus garvieae*, and *Edwardsiella tarda*).

As a result, as shown in FIGS. 9 to 12, when each peptide nucleic acid selected from among SEQ ID NO: 4 to SEQ ID NO: 7 was applied to bacterial DNA samples (*Streptococcus iniae, Streptococcus parauberis, Lactococcus garvieae* and *Edwardsiella tarda*), an amplification curve for each bacterial species and a melting curve graph for each fluorescence could be obtained. Furthermore, as shown in FIG. 13, when real-time PCR reactions for four bacterial species were performed at the same time in one tube, multi-detection of the four bacterial species (*Streptococcus iniae, Streptococcus parauberis, Lactococcus garvieae*, and *Edwardsiella tarda*) was possible by analysis of four melting curves.

Taking the above results together, it could be seen that individual detection of bacterial species or discrimination of bacterial species from a sample containing a mixture of different bacterial species was possible.

Example 3: Discrimination and Detection of Bacterial Species Based on Melting Fluorescence and Score at Each Temperature When bacterial species for unknown bacterial DNA samples are to be discriminated or detected using the PNA probes according to the present invention, a table listing scores at different melting temperatures as shown in Table 2 below can be previously prepared and can be used.

After melting curve analysis was performed as described in Example 2, the obtained fluorescent signal and $T_m$ value were digitized according to the temperature at which a perfect match appeared. Specifically, the range of perfect match temperature ±2° C. is made, and when the $T_m$ value for a unknown bacterial DNA sample is within this range, species in the bacterial sample can be identified and discriminated.

TABLE 2

| Fluorescent signals | PM (° C.) | Species in the bacterial samples |
| --- | --- | --- |
| FAM | 67 | *Edwardsiella tarda* |
| HEX | 63 | *Streptococcus parauberis* |
| TexasRed | 63 | *Streptococcus iniae* |
| Cy5 | 63 | *Lactococcus garvieae* |

INDUSTRIAL APPLICABILITY

According to the present invention, a genetic marker for discrimination and/or detection of each of *Edwardsiella tarda, Streptococcus iniae, Streptococcus parauberis* and *Lactococcus garvieae*, which cause fish diseases, and a peptide nucleic acid and a primer pair, which are specific for the genetic marker, are used to amplify and obtain melting curves having different fluorescences depending on bacterial species. Thus, bacteria that cause fish diseases can be discriminated in a simple, rapid and accurate manner, and whether or not fish would be infected with the bacteria can be detected.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A method for or detection of *Edwardsiella tarda*, comprising the steps of:

(a) extracting a target nucleic acid from a sample;

(b) amplifying a genetic marker nucleotide sequence for *Edwardsiella tarda* contained in the target nucleic acid, by use of a primer pair;

(c) hybridizing to the amplified genetic marker of step (b) a PNA probe for detection of *Edwardsiella tarda*, consisting of the nucleotide sequence of SEQ ID NO: 4;

(d) obtaining a temperature-dependent melting curve while increasing temperature of the PNA probe-hybridized product of step (c); and (e) analyzing the melting curve obtained in step (d) to determine a melting temperature, thereby detecting whether or not fish would be infected with *Edwardsiella tarda*.

2. The method of claim 1, wherein the primer pair consists of nucleotide sequences of SEQ ID NOs: 1 and 2.

3. The method of claim 1, wherein at least one of a reporter and a quencher is attached to the PNA probe.

* * * * *